(12) United States Patent
Sharma et al.

(10) Patent No.: US 7,834,295 B2
(45) Date of Patent: Nov. 16, 2010

(54) PRINTABLE IGNITERS

(75) Inventors: C. V. Krishnamohan Sharma, Santa Clara, CA (US); Hoi Sze Lau, Palo Alto, CA (US); Karen Wang, Cupertino, CA (US); Mingzu Lei, San Jose, CA (US); Vladimir Rappoport, Mountain View, CA (US)

(73) Assignee: Alexza Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 12/211,554

(22) Filed: Sep. 16, 2008

(65) Prior Publication Data

US 2010/0068154 A1    Mar. 18, 2010

(51) Int. Cl.
*F23Q 7/00* (2006.01)
*F02B 1/12* (2006.01)

(52) U.S. Cl. .................................. 219/260; 123/143 R

(58) Field of Classification Search ......... 219/260–270; 123/143 R–143 C
See application file for complete search history.

(56) References Cited

U.S. PATENT DOCUMENTS

| | | | |
|---|---|---|---|
| 3,150,020 A | 9/1964 | Kilmer | |
| 3,695,179 A | 10/1972 | Rainone et al. | |
| 3,791,302 A | 2/1974 | McLeod | |
| 3,792,302 A | 2/1974 | Downing et al. | |
| 3,831,606 A | 8/1974 | Damani | |
| 3,971,377 A | 7/1976 | Damani | |
| 3,982,095 A | 9/1976 | Robinson | |
| 4,013,061 A | 3/1977 | Trumble et al. | |
| 4,020,379 A | 4/1977 | Manning | |
| 4,045,156 A | 8/1977 | Chu et al. | |
| 4,047,483 A | 9/1977 | Williams | |

(Continued)

FOREIGN PATENT DOCUMENTS

DE    3542447 A1    6/1987

(Continued)

OTHER PUBLICATIONS

U.S. Appl. No. 12/628,949, filed Dec. 1, 2009, Zaffaroni et al.

(Continued)

*Primary Examiner*—Daniel Robinson
(74) *Attorney, Agent, or Firm*—Swanson & Bratschun, L.L.C.

(57) ABSTRACT

An igniter comprises at least two conductors in the spaced-apart configuration and an electrically conductive layer bridging the at least two conductors, wherein the conductive layer has an electrical resistance greater than an electrical resistance of the at least two conductors. In one embodiment, the at least two conductors and the electrically conductive layer comprise a conductive ink, which may be the same conductive ink having different dimensions. A supplementary initiator composition may be deposited on or incorporated into the conductive layer. In a process for producing the igniter, the electrically conductive layer and the at least two conductors are printed on a non-electrically conducting substrate. Also disclosed are a method for igniting a combustible composition using the igniter, a method for producing an aerosol drug using the igniter, a method for providing a dose of a drug to a human patient using the igniter, a drug delivery device comprising the igniter and a drug supply unit comprising the igniter.

33 Claims, 4 Drawing Sheets

U.S. PATENT DOCUMENTS

Figure 1A:
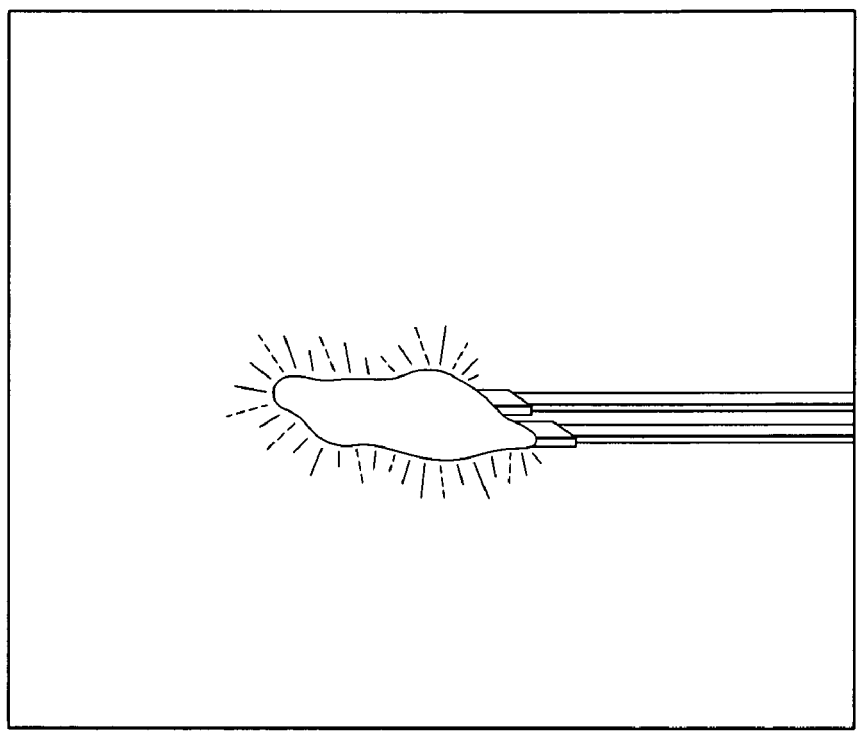

| | | | |
|---|---|---|---|
| 4,059,388 A | 11/1977 | Shaffer | |
| 4,189,200 A | 2/1980 | Yeager et al. | |
| 4,193,388 A | 3/1980 | Frosch et al. | |
| 4,236,544 A | 12/1980 | Osaka | |
| 4,354,432 A | 10/1982 | Cannavo' et al. | |
| 4,369,269 A | 1/1983 | Harper et al. | |
| 4,372,213 A | 2/1983 | Rozner et al. | |
| 4,374,686 A | 2/1983 | Davitt et al. | |
| 4,419,650 A | 12/1983 | John | |
| 4,443,495 A | 4/1984 | Morgan et al. | |
| 4,444,160 A * | 4/1984 | Steele | 123/179.21 |
| 4,476,378 A * | 10/1984 | Takizawa et al. | 219/270 |
| 4,508,755 A | 4/1985 | Reintjes et al. | |
| 4,549,071 A * | 10/1985 | Hatanaka et al. | 219/270 |
| 4,627,963 A | 12/1986 | Olson | |
| 4,700,629 A | 10/1987 | Benson et al. | |
| 4,708,151 A | 11/1987 | Shelar | |
| 4,714,082 A | 12/1987 | Banerjee et al. | |
| 4,756,318 A | 7/1988 | Clearman et al. | |
| 4,819,665 A | 4/1989 | Roberts et al. | |
| 4,854,331 A | 8/1989 | Banerjee et al. | |
| 4,881,556 A | 11/1989 | Clearman et al. | |
| 4,892,037 A | 1/1990 | Betts | |
| 4,935,073 A | 6/1990 | Bartlett et al. | |
| 4,989,619 A | 2/1991 | Clearman et al. | |
| 5,020,548 A | 6/1991 | Farrier et al. | |
| 5,027,707 A | 7/1991 | Mei | |
| 5,033,483 A | 7/1991 | Clearman et al. | |
| 5,042,509 A | 8/1991 | Banerjee et al. | |
| 5,060,666 A | 10/1991 | Clearman et al. | |
| 5,060,671 A | 10/1991 | Counts et al. | |
| 5,067,499 A | 11/1991 | Banerjee et al. | |
| 5,095,921 A | 3/1992 | Losee et al. | |
| 5,105,831 A | 4/1992 | Banerjee et al. | |
| 5,135,009 A | 8/1992 | Muller et al. | |
| 5,144,962 A | 9/1992 | Counts et al. | |
| 5,179,966 A | 1/1993 | Losee et al. | |
| 5,249,586 A | 10/1993 | Morgan et al. | |
| 5,269,327 A | 12/1993 | Counts et al. | |
| 5,285,798 A | 2/1994 | Banerjee et al. | |
| 5,322,018 A | 6/1994 | Hadden et al. | |
| 5,322,075 A | 6/1994 | Deevi et al. | |
| 5,345,951 A | 9/1994 | Serrano et al. | |
| 5,357,984 A | 10/1994 | Farrier et al. | |
| 5,407,473 A | 4/1995 | Miura et al. | |
| 5,408,574 A | 4/1995 | Deevi et al. | |
| 5,468,936 A | 11/1995 | Deevi et al. | |
| 5,479,948 A | 1/1996 | Counts et al. | |
| 5,505,214 A | 4/1996 | Collins et al. | |
| 5,509,354 A | 4/1996 | Dorffler et al. | |
| 5,538,020 A | 7/1996 | Farrier et al. | |
| 5,549,849 A | 8/1996 | Namura et al. | |
| 5,564,442 A | 10/1996 | MacDonald et al. | |
| 5,573,565 A | 11/1996 | Dalton et al. | |
| 5,584,701 A | 12/1996 | Lampotang et al. | |
| 5,591,368 A | 1/1997 | Fleischhauer et al. | |
| 5,593,792 A | 1/1997 | Farrier et al. | |
| 5,603,350 A | 2/1997 | Stoll et al. | |
| 5,613,504 A | 3/1997 | Collins et al. | |
| 5,613,505 A | 3/1997 | Campbell et al. | |
| 5,623,115 A | 4/1997 | Lauritzen et al. | |
| 5,626,360 A | 5/1997 | Lauritzen et al. | |
| 5,649,554 A | 7/1997 | Sprinkel et al. | |
| 5,672,843 A | 9/1997 | Evans et al. | |
| 5,686,691 A | 11/1997 | Hamilton et al. | |
| 5,845,933 A | 12/1998 | Walker et al. | |
| 5,865,185 A | 2/1999 | Collins et al. | |
| 5,878,752 A | 3/1999 | Adams et al. | |
| 5,890,908 A | 4/1999 | Lampotang et al. | |
| 6,053,176 A | 4/2000 | Adams et al. | |
| 6,062,210 A | 5/2000 | Welles | |
| 6,164,287 A | 12/2000 | White | |
| 6,190,326 B1 | 2/2001 | McKinnon et al. | |
| 6,289,813 B1 | 9/2001 | Duguet et al. | |
| 6,325,475 B1 | 12/2001 | Hayes et al. | |
| 6,328,033 B1 | 12/2001 | Avrahami | |
| 6,390,453 B1 | 5/2002 | Frederickson et al. | |
| 6,416,848 B2 * | 7/2002 | Sawamura | 428/209 |
| 6,478,903 B1 | 11/2002 | John, Jr. et al. | |
| 6,632,380 B1 | 10/2003 | Wessling | |
| 6,648,950 B2 | 11/2003 | Lee et al. | |
| 6,660,632 B2 | 12/2003 | Hill et al. | |
| 6,671,945 B2 | 1/2004 | Gerber et al. | |
| 6,680,668 B2 | 1/2004 | Gerber et al. | |
| 6,682,716 B2 | 1/2004 | Hodges et al. | |
| 6,684,880 B2 | 2/2004 | Trueba | |
| 6,713,399 B1 | 3/2004 | Kao | |
| 6,716,415 B2 | 4/2004 | Rabinowitz et al. | |
| 6,716,416 B2 | 4/2004 | Rabinowitz et al. | |
| 6,716,417 B2 | 4/2004 | Rabinowitz et al. | |
| 6,737,042 B2 | 5/2004 | Rabinowitz et al. | |
| 6,737,043 B2 | 5/2004 | Rabinowitz et al. | |
| 6,740,307 B2 | 5/2004 | Rabinowitz et al. | |
| 6,740,308 B2 | 5/2004 | Rabinowitz et al. | |
| 6,740,309 B2 | 5/2004 | Rabinowitz et al. | |
| 6,743,415 B2 | 6/2004 | Rabinowitz et al. | |
| 6,759,029 B2 | 7/2004 | Hale et al. | |
| 6,776,978 B2 | 8/2004 | Rabinowitz et al. | |
| 6,780,399 B2 | 8/2004 | Rabinowitz et al. | |
| 6,780,400 B2 | 8/2004 | Rabinowitz et al. | |
| 6,783,753 B2 | 8/2004 | Rabinowitz et al. | |
| 6,797,259 B2 | 9/2004 | Rabinowitz et al. | |
| 6,803,031 B2 | 10/2004 | Rabinowitz et al. | |
| 6,805,853 B2 | 10/2004 | Rabinowitz et al. | |
| 6,805,854 B2 | 10/2004 | Hale et al. | |
| 6,814,954 B2 | 11/2004 | Rabinowitz et al. | |
| 6,814,955 B2 | 11/2004 | Rabinowitz et al. | |
| 6,855,310 B2 | 2/2005 | Rabinowitz et al. | |
| 6,884,408 B2 | 4/2005 | Rabinowitz et al. | |
| 6,994,843 B2 | 2/2006 | Rabinowitz et al. | |
| 7,005,121 B2 | 2/2006 | Rabinowitz et al. | |
| 7,005,122 B2 | 2/2006 | Hale et al. | |
| 7,008,615 B2 | 3/2006 | Rabinowitz et al. | |
| 7,008,616 B2 | 3/2006 | Rabinowitz et al. | |
| 7,011,819 B2 | 3/2006 | Hale et al. | |
| 7,011,820 B2 | 3/2006 | Rabinowitz et al. | |
| 7,014,840 B2 | 3/2006 | Hale et al. | |
| 7,014,841 B2 | 3/2006 | Rabinowitz et al. | |
| 7,018,619 B2 | 3/2006 | Rabinowitz et al. | |
| 7,018,620 B2 | 3/2006 | Rabinowitz et al. | |
| 7,018,621 B2 | 3/2006 | Hale et al. | |
| 7,022,312 B2 | 4/2006 | Rabinowitz et al. | |
| 7,029,658 B2 | 4/2006 | Rabinowitz et al. | |
| 7,033,575 B2 | 4/2006 | Rabinowitz et al. | |
| 7,045,118 B2 | 5/2006 | Rabinowitz et al. | |
| 7,045,119 B2 | 5/2006 | Rabinowitz et al. | |
| 7,048,909 B2 | 5/2006 | Rabinowitz et al. | |
| 7,052,679 B2 | 5/2006 | Rabinowitz et al. | |
| 7,052,680 B2 | 5/2006 | Rabinowitz et al. | |
| 7,060,254 B2 | 6/2006 | Rabinowitz et al. | |
| 7,060,255 B2 | 6/2006 | Rabinowitz et al. | |
| 7,063,830 B2 | 6/2006 | Rabinowitz et al. | |
| 7,063,831 B2 | 6/2006 | Rabinowitz et al. | |
| 7,063,832 B2 | 6/2006 | Rabinowitz et al. | |
| 7,067,114 B2 | 6/2006 | Rabinowitz et al. | |
| 7,070,761 B2 | 7/2006 | Rabinowitz et al. | |
| 7,070,762 B2 | 7/2006 | Rabinowitz et al. | |
| 7,070,763 B2 | 7/2006 | Rabinowitz et al. | |
| 7,070,764 B2 | 7/2006 | Rabinowitz et al. | |
| 7,070,765 B2 | 7/2006 | Rabinowitz et al. | |
| 7,070,766 B2 | 7/2006 | Rabinowitz et al. | |
| 7,078,016 B2 | 7/2006 | Rabinowitz et al. | |
| 7,078,017 B2 | 7/2006 | Rabinowitz et al. | |
| 7,078,018 B2 | 7/2006 | Rabinowitz et al. | |

| | | |
|---|---|---|
| 7,078,019 B2 | 7/2006 | Rabinowitz et al. |
| 7,078,020 B2 | 7/2006 | Rabinowitz et al. |
| 7,087,216 B2 | 8/2006 | Rabinowitz et al. |
| 7,087,217 B2 | 8/2006 | Rabinowitz et al. |
| 7,087,218 B2 | 8/2006 | Rabinowitz et al. |
| 7,090,830 B2 | 8/2006 | Hale et al. |
| 7,094,392 B2 | 8/2006 | Rabinowitz et al. |
| 7,108,847 B2 | 9/2006 | Rabinowitz et al. |
| 7,115,250 B2 | 10/2006 | Rabinowitz et al. |
| 7,169,378 B2 | 1/2007 | Rabinowitz et al. |
| 7,402,777 B2 | 7/2008 | Ron et al. |
| 7,442,368 B2 | 10/2008 | Rabinowitz et al. |
| 7,445,768 B2 | 11/2008 | Rabinowitz et al. |
| 7,449,172 B2 | 11/2008 | Rabinowitz et al. |
| 7,449,173 B2 | 11/2008 | Rabinowitz et al. |
| 7,449,174 B2 | 11/2008 | Rabinowitz et al. |
| 7,449,175 B2 | 11/2008 | Rabinowitz et al. |
| 7,458,374 B2 | 12/2008 | Hale et al. |
| 7,465,435 B2 | 12/2008 | Rabinowitz et al. |
| 7,465,436 B2 | 12/2008 | Rabinowitz et al. |
| 7,465,437 B2 | 12/2008 | Rabinowitz et al. |
| 7,468,179 B2 | 12/2008 | Rabinowitz et al. |
| 7,470,421 B2 | 12/2008 | Rabinowitz et al. |
| 7,485,285 B2 | 2/2009 | Rabinowitz et al. |
| 7,488,469 B2 | 2/2009 | Rabinowitz et al. |
| 7,491,047 B2 | 2/2009 | Rabinowitz et al. |
| 7,498,019 B2 | 3/2009 | Hale et al. |
| 7,507,397 B2 | 3/2009 | Rabinowitz et al. |
| 7,507,398 B2 | 3/2009 | Rabinowitz et al. |
| 7,510,702 B2 | 3/2009 | Rabinowitz et al. |
| 7,513,781 B2 | 4/2009 | Galauner et al. |
| 7,524,484 B2 | 4/2009 | Rabinowitz et al. |
| 7,537,009 B2 | 5/2009 | Hale et al. |
| 7,540,286 B2 | 6/2009 | Cross et al. |
| 7,550,133 B2 | 6/2009 | Hale et al. |
| 7,581,540 B2 | 9/2009 | Hale et al. |
| 7,585,493 B2 | 9/2009 | Hale et al. |
| 7,601,337 B2 | 10/2009 | Rabinowitz et al. |
| 7,645,442 B2 | 1/2010 | Hale et al. |
| 2002/0000225 A1 | 1/2002 | Schuler et al. |
| 2002/0035945 A1 | 3/2002 | Knowlton et al. |
| 2002/0037437 A1 | 3/2002 | Yamamoto |
| 2002/0097139 A1 | 7/2002 | Gerber et al. |
| 2003/0015196 A1 | 1/2003 | Hodges et al. |
| 2003/0032638 A1 | 2/2003 | Kim et al. |
| 2003/0049025 A1 | 3/2003 | Neumann et al. |
| 2003/0051728 A1 | 3/2003 | Lloyd et al. |
| 2003/0062042 A1 | 4/2003 | Wensley et al. |
| 2003/0070738 A1 | 4/2003 | Hamilton |
| 2003/0118512 A1 | 6/2003 | Shen |
| 2003/0121906 A1 | 7/2003 | Abbott et al. |
| 2003/0131843 A1 | 7/2003 | Lu |
| 2003/0138508 A1 | 7/2003 | Novack et al. |
| 2003/0209240 A1 | 11/2003 | Hale et al. |
| 2004/0001048 A1 | 1/2004 | Kraus et al. |
| 2004/0009128 A1 | 1/2004 | Rabinowitz et al. |
| 2004/0035409 A1 | 2/2004 | Harwig et al. |
| 2004/0055504 A1 | 3/2004 | Lee et al. |
| 2004/0083919 A1 | 5/2004 | Hosey et al. |
| 2004/0096402 A1 | 5/2004 | Hodges et al. |
| 2004/0099266 A1 | 5/2004 | Cross et al. |
| 2004/0101481 A1 | 5/2004 | Hale et al. |
| 2004/0102434 A1 | 5/2004 | Hale et al. |
| 2004/0105818 A1 | 6/2004 | Every et al. |
| 2004/0162517 A1 | 8/2004 | Furst et al. |
| 2004/0178185 A1* | 9/2004 | Yoshikawa et al. .......... 219/270 |
| 2004/0234699 A1 | 11/2004 | Hale et al. |
| 2004/0234914 A1 | 11/2004 | Hale et al. |
| 2004/0234916 A1 | 11/2004 | Hale et al. |
| 2005/0034723 A1 | 2/2005 | Bennett et al. |
| 2005/0037506 A1 | 2/2005 | Hale et al. |
| 2005/0079166 A1 | 4/2005 | Damani et al. |
| 2005/0126562 A1 | 6/2005 | Rabinowitz et al. |
| 2005/0131739 A1 | 6/2005 | Rabinowitz et al. |
| 2005/0258159 A1* | 11/2005 | Hale et al. .................. 219/270 |
| 2005/0268911 A1 | 12/2005 | Cross et al. |
| 2006/0032496 A1 | 2/2006 | Hale et al. |
| 2006/0032501 A1 | 2/2006 | Hale et al. |
| 2006/0120962 A1 | 6/2006 | Rabinowitz et al. |
| 2006/0193788 A1 | 8/2006 | Hale et al. |
| 2006/0213897 A1* | 9/2006 | Annavarapu et al. ........ 219/270 |
| 2006/0257329 A1 | 11/2006 | Rabinowitz et al. |
| 2007/0122353 A1 | 5/2007 | Hale et al. |
| 2007/0140982 A1 | 6/2007 | Every et al. |
| 2007/0286816 A1 | 12/2007 | Hale et al. |
| 2008/0038363 A1 | 2/2008 | Zaffaroni et al. |
| 2008/0110872 A1 | 5/2008 | Hale et al. |
| 2008/0175796 A1 | 7/2008 | Rabinowitz et al. |
| 2008/0216828 A1 | 9/2008 | Wensley |
| 2008/0299048 A1 | 12/2008 | Hale et al. |
| 2008/0306285 A1 | 12/2008 | Hale et al. |
| 2008/0311176 A1 | 12/2008 | Hale et al. |
| 2009/0062254 A1 | 3/2009 | Hale et al. |
| 2009/0071477 A1 | 3/2009 | Hale et al. |
| 2009/0180968 A1 | 7/2009 | Hale et al. |
| 2009/0229600 A1 | 9/2009 | Hale et al. |
| 2009/0235926 A1 | 9/2009 | Cross |
| 2009/0246147 A1 | 10/2009 | Rabinowitz et al. |
| 2009/0258075 A1 | 10/2009 | Hale et al. |
| 2009/0301363 A1 | 12/2009 | Damani et al. |
| 2010/0006092 A1 | 1/2010 | Hale et al. |
| 2010/0055048 A1 | 3/2010 | Hale et al. |
| 2010/0065052 A1 | 3/2010 | Sharma et al. |
| 2010/0068154 A1 | 3/2010 | Sharma et al. |
| 2010/0068155 A1 | 3/2010 | Lei et al. |

FOREIGN PATENT DOCUMENTS

| | | |
|---|---|---|
| EP | 277519 A2 | 8/1988 |
| EP | 279796 A1 | 8/1988 |
| EP | 430559 A2 | 6/1991 |
| EP | 816674 A1 | 1/1998 |
| GB | 2049651 A | 12/1980 |
| WO | WO-9409842 A1 | 5/1994 |
| WO | WO-0066206 A2 | 11/2000 |
| WO | WO-03037412 A2 | 5/2003 |
| WO | WO-03095012 A1 | 11/2003 |
| WO | WO-2004104490 A1 | 12/2004 |
| WO | WO-2004104491 A2 | 12/2004 |
| WO | WO-2004104492 A2 | 12/2004 |
| WO | WO-2004104493 A2 | 12/2004 |
| WO | WO-2004106268 A2 | 12/2004 |

OTHER PUBLICATIONS

U.S. Appl. No. 12/789,044, filed May 27, 2010, Sharma et al.
De Yong et al. (1998) "Radiative Ignition of Pyrotechnics: Effect of Wavelength on Ignition Threshold" Propellants, Explosives, Pyrotechnics 23:328-332.
McCarthy, D.K., et al. (May, 1985) "Burn Front Velocity as a function of Pellet Density in Iron /Potassium Perchlorate Heat Powders" Sandia Report.
Reticulated Vitreous Carbon (1997) Flyer for ERG Materials and Aerospace Corp.
Frieser et al. (1980) Journal of Applied Electrochemistry 10:449-457, "Surface treatements of silicon to enhance thermal nucleation".
Merzhanov, Alexander G., (Aug. 19, 1994) "Pyrotechnical Aspects of Self-Propogating High-Temperature Synthesis" Russian Academy of Sciences: International Pyrotechnics Seminar Colorado Springs, US Jul. 25-29, 1994.
Peeters et al. (Jul. 1997)"Thermal Inkjet Technology" Circuits and Devices pp. 19-23.

* cited by examiner

PRINTABLE IGNITERS

TECHNICAL FIELD

This invention relates generally to igniters for rapid heating applications, such as aerosol drug delivery, deployment of pyrotechnics, and the like.

BACKGROUND

Igniters are an integral component of many devices, including automobile passenger restraint systems (airbags), seat belt tensioning devices, blasting charges for mining or construction, and the like. Unfortunately, many of the igniters currently available on the market have significant drawbacks with respect to ease and cost of manufacturing, as well as other issues. For example, many of the currently available igniters require the use of a bridge wire which must be soldered into place—a time-consuming, labor-intensive, and ultimately costly manufacturing step. As such, it is difficult for such igniters utilizing bridge wires to be efficiently and/or inexpensively mass-produced. The soldered-on bridge wires can be fairly easily dislodged and, as a result, the reliability of igniter performance is often unacceptably low. Furthermore, many of the currently available igniters are stand-alone devices which can be difficult to integrate with other electronic components.

In addition, many of the currently available igniters require the use of explosive or "energetic" materials. Handling and use of such materials can be dangerous and the manufacture of devices utilizing such materials is often governed by various state or federal regulations. Furthermore, igniters incorporating explosive or energetic materials can generate sparks and can require the presence of a heat shield and/or other protective measures to prevent multiple or uncontrolled ignitions that could lead to non-uniform heating of a supporting substrate.

Another drawback of previous igniters is that they typically require a high energy input. Prior art igniters had electrodes which were spaced relatively far apart, requiring more material and a higher actuation energy.

SUMMARY

We have developed an igniter that overcomes many of the drawbacks and disadvantages of previously known igniters. In some embodiments, the igniter of the present invention can be manufactured using simple and inexpensive printing processes known in the art. As such, the present igniter can be efficiently and inexpensively mass-produced. As a result of the use of printing technology in the igniter manufacturing process, the igniter of the present invention typically can be easily integrated with other electronic components, which can be printed on the same substrate as the subject igniter. In some embodiments, all components of the igniter are printed onto the substrate which can produce igniters with reliable performance. Furthermore, some embodiments of the igniter do not require the use of explosive or energetic materials. As such, the manufacturing of the present igniter is not subject to the same restrictions required by prior art explosive or energetic igniters.

The igniter of the present invention can be used in conjunction with a reactant composition that is capable of undergoing an exothermic chemical reaction upon actuation by the present igniter. Upon initiation, the igniter of the present invention typically produces a controlled, localized heat or "glow" (shown in FIG. 1A) that is very different from the display of sparks (shown in FIG. 1B) that is produced upon initiation of igniters that utilize explosive or energetic materials.

Many prior art igniters rely on sparks generated by the energetic materials to actuate the reactant. In order to localize the sparks to prevent multiple ignitions, a fiberglass shield is required. However, using the printable igniters of the present invention, no energetic materials are required. Instead, the actuation of the reactant relies on a localized heat source associated with the reactant. As a result, components (such as energetic materials and hence fiberglass heat shields can be eliminated) are needed.

An additional advantage of the production of a "glow" as opposed to the production of sparks is that the igniter can be in close proximity with the reactant composition that it is intended to actuate. This is especially important in applications where small device size is an advantage, such as handheld devices intended for the delivery of aerosolized drugs.

Accordingly, disclosed herein is an igniter comprising: a) at least two conductors, where the at least two conductors are in a spaced-apart configuration; and b) a conductive layer bridging the at least two conductors, where the conductive layer has an electrical resistance that is greater than an electrical resistance of both of the at least two conductors. As used herein, "bridging" is intended to mean an electrical communication and includes but is not limited to overlaying, underlying or abutting the conductors.

The at least two conductors typically comprise the same material. However, it is also contemplated herein that the conductors may comprise different materials. For example, the at least two conductors may comprise a metal selected from the group consisting of copper, silver, gold, aluminum, titanium, nickel, iron, chromium, zinc, silicon, and combinations thereof. Alternatively, the at least two conductors may comprise a conductive polymer, an allotrope of carbon, or a conductive ink comprising particles in combination with a binder, optionally in combination with a solvent. The at least two conductors are typically the same thickness. However, it is also contemplated herein that the conductors may comprise different thicknesses. The thickness of the conductors may be less than 1 mm, and is preferably less than about 200 μm.

The at least two conductors are in a spaced-apart configuration. As used herein, the term "spaced-apart configuration" means that some space exists between the at least two conductors. The space may be open or filled (or partially filled) with another substance. The conductors are typically linear and aligned parallel to each other, but may have any shape or orientation. Typically, the spacing between the conductors is within the range of about 2 μm to about 2 mm; in other embodiments the spacing is within the range of about 10 μm to about 500 μm; in other embodiments the spacing is less than 150 μm. The conductors can overlap each other, provided that a space is maintained between the conductors.

In many embodiments the at least two conductors have the same resistance. However, it is contemplated herein that the at least two conductors may have different resistances.

The conductive layer has an electrical resistance that is greater than the electrical resistance of the at least two conductors. The conductive layer may comprise a conductive ink, which is deposited across the at least two conductors using a printing process, such as (for example and not by way of limitation), inkjet printing, flexography, offset printing, gravure printing, screen printing, tip dispensing, Meyer Bar, electrophotographic printing, pad printing (i.e., stamping) and lithography. An inkjet printing process selected from the group consisting of piezoelectric ejection, thermal ejection, acoustic ejection, and ultrasonic nozzle dispensing, may be used to deposit the conductive ink across the at least two conductors.

A conductive ink may comprise particles in combination with a binder. In some embodiments, the particles are carbon-comprising particles or metal particles. Carbon-comprising particles may comprise a material selected from the group consisting of carbon, activated carbon, graphite, carbon nanotubes, fullerenes, and combinations thereof. Alternatively, the conductive ink may comprise non-carbon particles, which may be metal particles.

The binder may be an organic, an inorganic, or a combination organic/inorganic material. The binder can be a homopolymer or a multipolymer. Some examples of binders include thermoset resins, thermoplastic resins, or combinations thereof. Some examples of thermoplastic resins include, but are not limited to, polyethylene, polypropylene, polyamide, polyurethane, polyvinyl chloride, and thermoplastic polyester resin. Examples of thermoset resins include, but are not limited to, thermoset polyester resins and epoxy resins. Some examples of water-soluble polymers in water-based systems include, but are not limited to, poly(vinyl alcohol), poly(vinyl pyrrolidone), gelatin, cellulose ethers (such as hydroxypropyl cellulose or hydroxypropyl methyl cellulose) poly(oxazolines), poly(vinylacetamides), partially hydrolyzed poly(vinyl acetate/vinyl alcohol), poly(acrylic acid), poly(acrylamide), poly(alkylene oxide), sulfonated or phosphated polyesters and polystyrenes, casein, zein, albumin, chitin, chitosan, dextran, pectin, collagen derivatives, collodian, agar-agar, arrowroot, guar, carrageenan, tragacanth, xanthan, rhamsan, and the like. Inorganic binders include clays, silicates, phosphates, aluminates, and combinations thereof.

Optionally, the conductive ink may also include a solvent, which may be one of many organic, aqueous, or non-aqueous solvents known in the art. Examples of such solvents include (without limitation) halocarbons, alcohols, cyclic ethers, nitriles, amides, esters, acids, acetates, ketones, chlorocarbons, alkanes, ethers, sulfoxides, monomers of polymeric compounds, and water.

In another alternative embodiment, the conductive layer comprises a conductive organic material, such as a conductive polymer.

The igniter of the invention typically further comprises a source of electrical power. The source of electrical power may be, for example and not by way of limitation, a battery, a capacitor, or a power supply.

In one embodiment the conductive layer is capable of self-ignition upon the application of a voltage less than 25 V. In another embodiment the conductive layer self-ignites upon the application of voltage within the range of about 1 V to about 20 V. In yet another embodiment the conductive layer self-ignites upon application of a voltage within the range of about 1 V to about 15 V.

The conductive layer may have a resistance within the range of about 1 Ω to about 100 Ω; and embodiments include resistance within the range of about 2 Ω to about 20 Ω. The conductive layer may have a resistivity of less than 250 Ω/square/mil; more typically, less than 100 Ω/square/mil.

In one embodiment the conductive layer has a thickness within the range of about 1 μm to about 100 μm; other embodiments may have a thickness within the range of about 4 μm to about 20 μm. Embodiments include the conductive layer having a length within the range of about 5 μm to about 5 mm. Other embodiments have a conductive layer with a length within the range of about 10 μm to about 3 mm.

The igniter of the invention may further comprise a substrate. In some embodiments, one or more components of the igniter is typically in contact with or otherwise supported by the substrate. For example, one or more of the at least two conductors may be in contact with the substrate, with the conductive layer printed across the at least two conductors. Alternatively, the conductive layer may be printed on the substrate, with the at least two conductors provided across the conductive layer.

The substrate may comprise a material that has low conductivity or is non-conductive, which is typically selected from the group consisting of ceramics, glasses, synthetic polymers, and composite materials. The substrate may comprise a synthetic polymer selected from the group consisting of polyesters and polyimides. Alternatively, the low conductivity or non-conductive material may comprise a composite material selected from the group consisting of epoxy resin-bonded glass fabrics (ERBGFs) and fluorocarbon laminate materials. In one embodiment the substrate is planar. The substrate may have a thickness within the range of about 0.5 mil to about 20 mil. In other embodiments the thickness is within the range of about 1 mil to about 5 mil.

Although the use of initiator compositions or other energetic materials is not required to practice the present invention, in certain embodiments (for example, when it is desired to produce greater thermal output, i.e., a hotter spark or glow, or to further lower the energy requirements of the igniter), the igniter of the invention may comprise a supplementary initiator composition, where the supplementary initiator composition is in contact with at least a portion of the conductive layer.

The supplementary initiator composition may be incorporated into the igniter of the invention in a number of ways. The supplementary initiator composition may be deposited as a separate layer over the conductive layer. In such an embodiment, the supplementary initiator composition is typically deposited to have a thickness within the range of about 1 μm to about 100 μm. Alternatively, the supplementary initiator composition may be co-formulated with the conductive layer, for example, by admixing the supplementary initiator composition with the conductive layer material prior to printing the conductive layer/initiator composition onto the substrate surface. In this embodiment, the supplementary initiator composition may comprise within the range of about 1% to about 50% of the total weight of the conductive layer/initiator composition. In other embodiments, the supplementary initiator composition comprises within the range of about 5% to about 30% of the total weight of the conductive layer/initiator composition.

The supplementary initiator composition may comprise energetic materials, which could include at least one oxidizing agent and at least one metal reducing agent. The oxidizing agent may be oxygen, an oxygen-based gas, a solid oxidizing agent, or a combination thereof. In one embodiment, the oxidizing agent is a metal-containing oxidizing agent, which may comprise a perchlorate, chlorate, metal oxide, or an organic binder. In a particular embodiment, the metal-containing oxidizing agent is a perchlorate or chlorate of an alkali metal or an alkaline earth metal selected from the group consisting of potassium perchlorate ($KClO_4$), potassium chlorate ($KClO_3$), lithium perchlorate ($LiClO_4$), sodium perchlorate ($NaClO_4$), magnesium perchlorate ($Mg(ClO_4)_2$), and combinations thereof. In another embodiment, the metal-containing oxidizing agent is a metal oxide selected from the group consisting of $MoO_3$, $Fe_2O_3$, $Fe_3O_4$, $V_2O_5$, $CrO_3$, $Cr_2O_3$, $MnO_2$, $CO_3O_4$, $Ag_2O$, $CuO$, $WO_3$, $MgO$, $Nb_2O_5$, $MgAl_2O_4$, $Ce_2O_3$, and combinations thereof.

The metal reducing agent may be selected from the group consisting of molybdenum, magnesium, calcium, strontium, barium, boron, titanium, zirconium, vanadium, niobium, tantalum, chromium, tungsten, manganese, iron, cobalt, nickel, copper, zinc, cadmium, tin, antimony, bismuth, aluminum, silicon, and combinations thereof. Preferably, the metal reducing agent is aluminum, zirconium, titanium, or a combination thereof.

The igniter of the present invention is useful in aerosol drug delivery devices, explosive deployment devices, gas releasing devices, and pyrotechnic devices (for example, and not by way of limitation).

Also disclosed herein is a process for producing an igniter, comprising the steps of: a) providing at least two conductors in a spaced-apart configuration, and b) providing an electrically conductive layer bridging the conductors, where the conductive layer has an electrical resistance greater than the electrical resistance of the conductors.

The process may further include providing a source of electrical power in contact with the conductors and/or a switch to initiate the igniter. The source of electrical power may be, for example and not by way of limitation, a battery, a capacitor, or a power supply.

Also disclosed herein is a method for igniting a combustible composition, comprising the steps of: a) providing an igniter comprising: i) at least two conductors in a spaced-apart configuration, and ii) an electrically conductive layer bridging the conductors, where the conductive layer has an electrical resistance greater than the electrical resistance of the conductors; b) placing the igniter into an effective proximity with a combustible composition; and c) initiating of the igniter. Initiation of the igniter may be triggered by a signal, including (for example, and not by way of limitation) a sensor which is sensitive to motion, inhalation, vibration, or light; a timer; or a switch, which may be a manual switch or an electrical signal.

Also disclosed herein is a method for producing a vapor or an aerosol of a drug, comprising the steps of: a) providing an igniter comprising: i) at least two conductors in a spaced-apart configuration, and ii) an electrically conductive layer bridging the conductors, where the conductive layer has an electrical resistance greater than the electrical resistance of the conductors; b) providing a drug supply unit having a heating unit comprising an enclosure comprising a substrate having an exterior surface, where a drug is disposed on a portion of the exterior surface, and a reactant composition capable of undergoing an exothermic reaction disposed within the enclosure; c) placing the igniter into an effective proximity with the reactant composition; and d) actuating the reactant composition by initiating the igniter, thereby producing a vapor of the drug which can be allowed to condense to form an aerosol of the drug.

Also disclosed herein is a method for providing a dose of a drug to a subject (e.g., a human patient), comprising the steps of: a) providing an igniter comprising: i) at least two conductors in a spaced-apart configuration, and ii) an electrically conductive layer bridging the conductors, where the conductive layer has an electrical resistance greater than an electrical resistance of the conductors; b) providing a drug supply unit having a heating unit comprising an enclosure comprising a substrate having an exterior surface, where a drug is disposed on a portion of the exterior surface, and a reactant composition capable of undergoing an oxidation-reduction reaction disposed within the enclosure; c) placing the igniter into an effective proximity with the reactant composition; d) actuating the reactant composition by initiating the igniter, thereby producing an aerosol of the drug; and e) providing at least one dose of the drug aerosol to the patient. In one embodiment, actuation of the device is triggered by inhalation of the patient.

Also disclosed herein is a drug delivery device comprising an igniter comprising: a) at least two conductors in a spaced-apart configuration, and b) an electrically conductive layer bridging the conductors, where the conductive layer has an electrical resistance greater than an electrical resistance of the conductors.

Also disclosed herein is a drug supply unit for use in a drug delivery device, where the drug supply unit comprises an igniter comprising: a) at least two conductors in a spaced-apart configuration, and b) an electrically conductive layer bridging the conductors, where the conductive layer has an electrical resistance greater than an electrical resistance of the conductors.

Additional objects, advantages and novel features of the invention will be set forth in part in the description which follows, and in part will become apparent to those skilled in the art upon examination of the following, or may be learned by practice of the invention.

BRIEF DESCRIPTION OF THE DRAWINGS

Further features and advantages will become apparent from the following description of various embodiments of the invention, as illustrated in the accompanying drawings in which:

FIG. 1A shows the "glow" or localized heat generated by the igniter of the present invention.

FIG. 1B shows the sparks which are characteristically generated by a prior art bridge-wire igniter.

FIG. 2 is a schematic perspective view of an igniter showing the relative dimensions and spacing of a conductive layer and at least two conductors on a substrate.

FIG. 3A is a schematic perspective view of an embodiment of an igniter in which a conductive layer is printed across two parallel conductors on a substrate.

FIG. 3B is a schematic perspective view of an embodiment of an igniter in which a conductive ink (which has been previously admixed with a supplementary initiator composition) is printed across two parallel conductors, which comprise a conductive ink on a substrate.

FIG. 3C is a schematic perspective view of an embodiment of an igniter in which a supplementary initiator composition is printed across a conductive layer, which in turn has been printed across two parallel conductors, which comprise a conductive ink on a substrate.

FIG. 3D is a schematic perspective view of an embodiment of an igniter with conductors printed on a substrate and a conductive layer printed across the conductors.

FIG. 4 is a schematic perspective view of an embodiment of an igniter in which a conductive layer is sandwiched between two opposing L-shaped conductors which comprise a conductive ink on a substrate.

FIG. 5 is a schematic perspective view of an embodiment of an igniter in which a conductive layer is printed across two parallel conductors which comprise a conductive ink.

FIG. 6 is a cross-sectional side view of a heating unit for use in a drug delivery device or a drug supply unit.

DETAILED DESCRIPTION

Disclosed herein is a printable igniter for rapid heating applications, a process for producing the igniter, and methods for igniting a combustible composition, producing an aerosol of a drug, and providing a dose of a drug to a human patient using the igniter of the invention. Also disclosed herein are a drug delivery device and a drug supply unit incorporating the igniter of the present invention.

As used herein, the term "printable igniter" refers to an igniter wherein at least one or more of the components of the igniter is rendered on a substrate by any process applying a component to the surface including, but not limited to, a printing process, stamping, etching, drawing, brushing and painting A printing process in particular includes (for example and not by way of limitation), inkjet printing, flexography, offset printing, gravure printing, screen printing, tip dispensing, Meyer Bar, electrophotographic printing, pad printing (i.e., stamping), and lithography.

I. Definitions and Overview

Before the present invention is described in detail, it is to be understood that, unless otherwise indicated, this invention is not intended to be limited to specific applications such as airbags, inhalers, or the like, as such may vary. It is also to be understood that the terminology used herein is for the purpose of describing particular embodiments only, and is therefore not intended to limit the scope of the present invention.

It must be noted that, as used herein and in the claims, the singular forms "a," "and", and "the" include plural referents, unless the context clearly dictates otherwise. Thus, for example, reference to "an oxidizer" includes one or more oxidizers; reference to "a conductive ink" includes one or more conductive inks, and so forth.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The components of various embodiments of the igniter of the present invention, and methods for making and using the igniter, are described in detail below.

II. Igniter Components

A. Conductors

Any conductor known in the art can be utilized in the present igniter. The type of conductor used in the igniter is not particularly limiting, as long as the resistance of both of the conductors is less than the resistance of the conductive layer, and is stable to humidity and air and normal ambient temperatures. In many embodiments, the resistance of the conductive layer is at least twice the resistance of both of the conductors. The at least two conductors may have the same resistance. However, it is contemplated herein that the at least two conductors may have different resistances.

In the igniter of the present invention, the at least two conductors may be the same thickness. However, it is also contemplated herein that the conductors may have different thicknesses. The thickness of the conductors in some embodiments is less than 1 mm, and in some embodiments may be less than about 200 µm.

The at least two conductors are in a spaced-apart configuration. The conductors are typically aligned parallel to each other. The conductors can overlap each other, provided that a space is maintained between the conductors.

Figure 2:
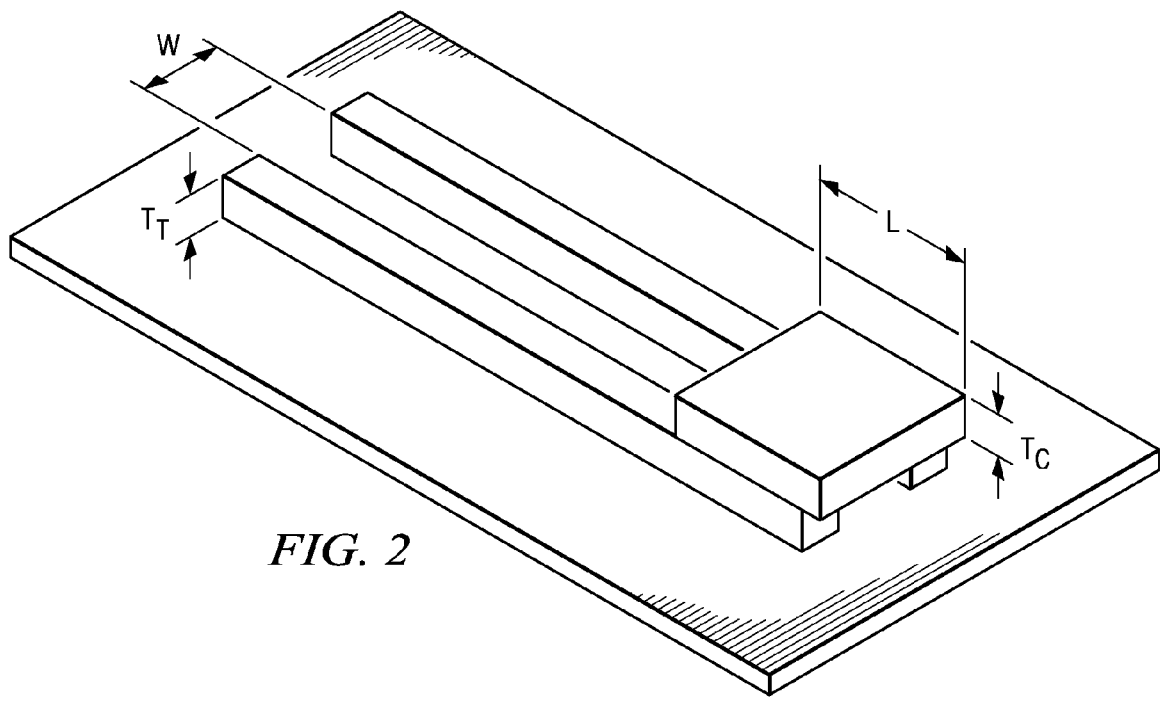

FIG. 2 shows the relative dimensions and spacing of the at least two conductors on a substrate for certain embodiments of the present invention. The spacing (shown as W in FIG. 2) between the conductors may be within the range of about 2 µm to about 2 mm; in certain embodiments within the range of about 10 µm to about 500 µm; in other embodiments less than 150 µm. Minimizing the spacing between the conductors minimizes the actuation energy requirement.

In some embodiments the at least two conductors comprise a metal selected from the group consisting of copper, silver, gold, aluminum, titanium, nickel, iron, chromium, zinc, silicon, and combinations thereof. As used herein, the term "metal" is intended to encompass not only pure metals, but also metal alloys, such as stainless steel, and metal oxides, such as indium tin oxide.

Alternatively, the at least two conductors may comprise a conductive polymer or an allotrope of carbon. Representative examples of suitable conductive polymers include, without limitation, PEDOT:PSS (Poly(3,4-ethylenedioxythiophene) poly(styrenesulfonate)) or polyaniline, and the like.

Alternatively, the conductors may comprise a conductive ink. The conductive ink can be rendered on the substrate by any known printing operation, including but not limited to, a printing process, stamping, etching, drawing, brushing and painting. In one embodiment the conductive ink is deposited on a substrate using a printing process, such as (for example and not by way of limitation), inkjet printing, flexography, offset printing, gravure printing, screen printing, tip dispensing, Meyer Bar, electrophotographic printing, pad printing (i.e., stamping), and lithography. Screen printing is a suitable printing process.

As used herein, the term "conductive ink" refers to an ink that can conduct electricity. Such inks are well-known in the art and may comprise a liquid formulation or slurry of particles. Once deposited, all or part of the ink solidifies (e.g., by drying). The term "conductive ink" is intended to encompass conductive inks and/or conductive paints in any of their various physical forms, including (for example and not by way of limitation) liquid formulations, slurries, or solidified (e.g., dried) layers of ink.

The conductive ink may comprise particles in combination with a binder. In one embodiment the particles are carbon-comprising particles, which comprise a material selected from the group consisting of carbon, activated carbon, graphite, carbon nanotubes, fullerenes, and combinations thereof. Representative examples of carbon particulate-containing inks include, without limitation, those available from Engineered Conductive Materials (Delaware, Ohio); Coates Electrographics (Midsomer Norton, England); Creative Materials (Tyngsboro, Mass.); and Alfa Aesar (Ward Hill, Mass.). Alternatively, the conductive ink may comprise non-carbon particles, which may be metal particles.

The binder may be an organic, an inorganic, or a combination organic/inorganic material. The binder can be a homopolymer or a multipolymer. Some representative binders include thermoplastic resins, thermoset resins, water-soluble polymers, or combinations thereof. Examples of thermoplastic resins include, but are not limited to, polyethylene, polypropylene, polyamide, polyurethane, polyvinyl chloride, and thermoplastic polyester resin. Examples of thermoset resins include, but are not limited to, thermoset polyester resins and epoxy resins. Examples of water-soluble polymers in water-based systems include, but are not limited to, poly(vinyl alcohol), poly(vinyl pyrrolidone), gelatin, cellulose ethers (such as hydroxypropyl cellulose or hydroxypropyl methyl cellulose), poly(oxazolines), poly(vinylacetamides), partially hydrolyzed poly(vinyl acetate/vinyl alcohol), poly(acrylic acid), poly(acrylamide), poly(alkylene oxide), sulfonated or phosphated polyesters and polystyrenes, chitin, chitosan, dextran, collagen derivatives, collodian, agar-agar, arrowroot, xanthan, and the like. Inorganic binders include clays, silicates, phosphates, aluminates, and combinations thereof.

The conductive ink may also include a solvent, which may be one of many organic, aqueous, or non-aqueous solvents known in the art. Examples of such solvents include (without limitation) halocarbons, alcohols, cyclic ethers, nitriles, amides, esters, acids, acetates, ketones, chlorocarbons, alkanes, ethers, sulfoxides, monomers of polymeric compounds, water, and combinations thereof.

In one embodiment, the conductors comprise the same conductive ink as the conductive layer, as long as the resistance of the conductors is less than that of the conductive layer. This can be achieved (for example and not by way of limitation) by depositing the conductors to have a thickness (shown as $T_T$ in FIG. 2) that is greater than the thickness of the conductive layer (shown as $T_C$ in FIG. 2).

The at least two conductors may comprise the same material. However, it is also contemplated herein that the conductors may comprise different materials. For example, a first conductor may comprise copper, while the second conductor comprises silver.

B. Conductive Layer Compositions

The conductive layer has a resistance that is greater than the resistance of both of the at least two conductors. As such, the conductive layer can also be considered a "resistive layer".

In some embodiments the resistance of the conductive layer is at least two times that of the conductors. In order to avoid the needless expenditure of energy, the difference in resistance between the conductive layer and the conductors should be maximized as much as is practical. For example, the conductive layer may have a resistance within the range of about 1 Ω to about 100 Ω; in other embodiments within the range of about 2 Ω to about 20 Ω, and a resistivity of less than 250 Ω/square/mil, and in some embodiments less than 100 Ω/square/mil.

The conductive layer is may be adapted to initiate and produce a "glow" or localized heat upon application of electrical power. Upon initiation of the conductive layer, heat from the exothermic oxidation of the conductive layer composition is generated sufficient to actuate a reactant composition, e.g., a reactant composition-coated substrate.

The glow is a visual manifestation of the localized heating that is occurring and indicates the attainment of temperatures above 300° C., and in some embodiments above 400° C. Furthermore, the glow intensity represents the amount of conductive layer (or the surface area of the conductive layer) that oxidizes or glows in a given time. Therefore, depending upon the auto-ignition characteristics of the reactant composition, the heat output of the printable igniter (and/or glow intensity) can be determined. In some embodiments, the reactants may be initiated under 300° C., in which case the glow may not be critical to initiating the reactants. In some embodiments, the exposure time of the sustainable heat or glow is critical to initiating the reactants. Those skilled in the art can determine local heat or glow intensity required to initiate a particular reactant composition simply by optimizing the applied voltage, composition of the conductive layer, configuration of the conductive layer, and reactant composition coating parameters.

The conductive layer may be capable of self-ignition upon the application of a voltage less than 25 V. In some embodiments within the range of about 1 V to about 20 V; in other embodiments within the range of about 1 V to about 15 V. As used herein, the terms "self-ignition" and "self-ignites" refer to conductive materials that are capable of initiating without the presence of energetic or explosive materials.

The conductive layer of the present invention may self-ignite within less than 10 second of initiation of the igniter; in other embodiments within less than 1 second of initiation. The conductive layer self-igniting within less than 500 milliseconds and even within about 0.05 to about 100 milliseconds of initiation are provided in other embodiments.

The appropriate selection of the compositions adapted to initiate upon application of electrical power can be at least in part determined by the current of the power source, the desired self-ignition temperature, and/or the desired initiation time.

In one embodiment the conductive layer comprises a conductive ink. The conductive ink can be rendered on the substrate by any known printing operation, including but not limited to, a printing process, stamping, etching, drawing, brushing and painting. In one embodiment the conductive ink is deposited across the at least two conductors using a printing process, such as (for example and not by way of limitation), inkjet printing, flexography, offset printing, gravure printing, screen printing, tip dispensing, Meyer Bar, electrophotographic printing, pad printing (i.e., stamping), and lithography. An inkjet printing process may be selected from the group consisting of piezoelectric ejection, thermal ejection, acoustic ejection, and ultrasonic nozzle dispensing, is used to deposit the conductive ink across the at least two conductors.

The conductive ink may comprises particles in combination with a binder. The particles may be carbon-comprising particles, which may comprise a material selected from the group consisting of carbon, activated carbon, graphite, carbon nanotubes, fullerenes, and combinations thereof. Representative examples of carbon particulate-containing inks include, without limitation, those available from Engineered Conductive Materials (Delaware, Ohio); Coates Electrographics, (Midsomer Norton, England); Creative Materials (Tyngsboro, Mass.); and Alfa Aesar (Ward Hill, Mass.). Alternatively, the conductive ink may comprise non-carbon particles, which may be metal particles.

The binder may be an organic, an inorganic, or a combination organic/inorganic material. The binder can be a homopolymer or a multipolymer. Some preferred binders include thermoplastic resins, thermoset resins, water-soluble polymers, or combinations thereof. Examples of thermoplastic resins include, but are not limited to, polyethylene, polypropylene, polyamide, polyurethane, polyvinyl chloride, and thermoplastic polyester resin. Examples of thermoset resins include, but are not limited to, thermoset polyester resins and epoxy resins. Examples of water-soluble polymers in water-based systems include, but are not limited to, poly (vinyl alcohol), poly(vinyl pyrrolidone), gelatin, cellulose ethers (such as hydroxypropyl cellulose or hydroxypropyl methyl cellulose), poly(oxazolines), poly(vinylacetamides), partially hydrolyzed poly(vinyl acetate/vinyl alcohol), poly (acrylic acid), poly(acrylamide), poly(alkylene oxide), sulfonated or phosphated polyesters and polystyrenes, chitin, chitosan, dextran, collagen derivatives, collodian, agar-agar, arrowroot, xanthan, and the like. Inorganic binders include clays, silicates, phosphates, aluminates, and combinations thereof.

The conductive ink may also include a solvent, which may be one of many organic, aqueous, or non-aqueous solvents known in the art. Examples of such solvents include (without limitation) halocarbons, alcohols, cyclic ethers, nitriles, amides, esters, acids, acetates, ketones, chlorocarbons, alkanes, ethers, sulfoxides, monomers of polymeric compounds, water, and combinations thereof.

As discussed above, the conductive layer may comprise the same conductive ink as the conductors, as long as the resistance of the conductive layer is greater than that of the conductors. This can be achieved (for example, and not by way of limitation) by depositing the conductors to have a greater thickness than the conductive layer.

In another alternative embodiment, the conductive layer comprises a conductive organic material, such as a conductive polymer which may be in the form of a conductive ink. Representative examples of suitable conductive polymers include, without limitation, PEDOT:PSS (Poly(3,4-ethylenedioxythiophene) poly(styrenesulfonate)) or polyaniline, and the like.

Referring again to FIG. 2, the conductive layer dimensions include length and thickness. A longer, thicker conductive layer includes a greater amount of conductive material. The volume of conductive material in the conductive layer is related to the energy requirements of the igniter, where a higher volume has greater energy requirements. In some embodiments the conductive layer has a thickness ($T_C$) within the range of about 1 μm to about 100 μm; in other embodiments within the range of about 4 μm to about 20 μm. The conductive layer may have a length within the range of about 5 μm to about 5 mm; and in some embodiments within the range of about 10 μm to about 3 mm.

C. Substrates

The igniter of the invention further comprises a substrate. In some embodiments, one or more components of the igniter is in contact with or otherwise supported by the substrate. For example, one or more of the at least two conductors may be in contact with the substrate, then the conductive layer printed across the at least two conductors. Alternatively, the conductive layer may be printed on the substrate, then the at least two conductors provided over the conductive layer.

The substrate preferably comprises a material that has low conductivity or is non-conductive. The substrate may be selected from the group consisting of ceramics, glasses, synthetic polymers, and composite materials. The substrate may comprise a synthetic polymer selected from the group consisting of polyesters (e.g., polyethylene terephthalate) and polyimides (e.g., KAPTON® polyimide film, available from DuPont, Wilmington, Del.). Alternatively, the low conductivity or non-conductive material may comprise a composite material selected from the group consisting of epoxy resin-bonded glass fabrics (ERBGFs, e.g., FR4, available from JJ Orly, Clark, N.J.) and fluorocarbon laminate materials.

The geometry of the substrate can be any geometry or topology that allows a desired spatial arrangement of conductors, conductive layers, and optional supplementary initiator composition in contact with the conductive layer, having the characteristics required for a particular application. In many embodiments the substrate is planar. In one embodiment, the substrate has a rectangular planar configuration allowing a placement of spaced conductors longitudinally, with a conductive layer across and in contact with the conductors. In another embodiment, the substrate has a vertical component which allows placement of spaced conductors vertically. In such embodiment, for example, one or more of the conductors may be supported by, but not actually in direct contact with, the substrate.

The substrate may be continuous but, in some embodiments, the substrate can have interruptions, perforations, or other discontinuities. For example, in one embodiment, a slit is formed in the substrate to facilitate heating of both sides of the substrate to a uniform temperature.

In many embodiments the substrate is the same thickness throughout. However, it is also contemplated herein that different portions of the substrate may comprise different thicknesses. By way of example, the substrate can have a thickness within the range of about 0.5 mil to about 20 mil; with a the range of about 1 mil to about 5 mil being preferred in some embodiments.

D. Supplementary Initiator Compositions

Use of an igniter in which the conductive layer comprises a composition that is adapted to initiate upon application of electrical power allows initiation without a supplementary initiator composition. However, in certain embodiments, the igniter of the present invention may comprise a supplementary initiator composition, where the supplementary initiator composition is in contact with at least a portion of the conductive layer. A supplementary initiator composition may be used (for example and not by way of limitation) when it desired to produce a hotter spark or greater thermal output, or to further lower the energy requirements of the igniter.

A wide variety of supplementary initiator compositions can be used in conjunction with the present igniter. The supplementary initiator composition to be utilized can be selected based on the intended use of the igniter.

Supplementary initiator compositions can be optimized to provide the desired thermal output and sparking intensity. Preferred supplementary initiator compositions deflagrate and produce an intense spark that readily and reliably actuates a reactant composition, but does not damage the surface of the reactant composition.

The supplementary initiator composition typically comprises energetic materials. As used herein, the term "energetic materials" refers to any materials which, when used in combination, are capable of undergoing an exothermic chemical reaction.

The energetic materials of the supplementary initiator composition may include at least one oxidizing agent and at least one metal reducing agent. The oxidizing agent may be oxygen, an oxygen-based gas, a oxidizing agent, or a combination thereof. In one embodiment, the oxidizing agent is a metal-containing oxidizing agent, which typically comprises a perchlorate, chlorate, metal oxide, or an organic binder. In a particular embodiment, the metal-containing oxidizing agent is a perchlorate or chlorate of an alkali metal or an alkaline earth metal selected from the group consisting of potassium perchlorate ($KClO_4$), potassium chlorate ($KClO_3$), lithium perchlorate ($LiClO_4$), sodium perchlorate ($NaClO_4$), magnesium perchlorate ($Mg(ClO_4)_2$), and combinations thereof. In another embodiment, the metal-containing oxidizing agent is a metal oxide selected from the group consisting of $MoO_3$, $Fe_2O_3$, $Fe_3O_4$, $V_2O_5$, $CrO_3$, $Cr_2O_3$, $MnO_2$, $CO_3O_4$, $Ag_2O$, $CuO$, $WO_3$, $MgO$, $Nb_2O_5$, $MgAl_2O_4$, $Ce_2O_3$, and combinations thereof. In certain embodiments, the oxidizing agent includes more than one oxidizing agent.

The metal reducing agent may be selected from the group consisting of molybdenum, magnesium, calcium, strontium, barium, boron, titanium, zirconium, vanadium, niobium, tantalum, chromium, tungsten, manganese, iron, cobalt, nickel, copper, zinc, cadmium, tin, antimony, bismuth, aluminum, silicon, and combinations thereof. In some embodiments the metal reducing agent is aluminum, zirconium, titanium, or a combination thereof. In certain embodiments, the metal reducing agent includes more than one metal reducing agent.

In certain embodiments, the metal reducing agent and the oxidizing agent can be in the form of a powder. The term "powder" refers to powders, particles, prills, flakes, and any other particulate that exhibits an appropriate size and/or surface area to sustain self-propagating ignition. For example, in certain embodiments, the powder can comprise particles exhibiting an average diameter ranging from 0.01 µm to 200 µm.

In certain other embodiments, reliable, reproducible, and controlled actuation of the reactant composition can be facilitated by the use of a supplementary initiator composition comprising a mixture of at least one oxidizing agent, at least one metal reducing agent, and at least one binder and/or additive material, such as a gelling agent and/or binder. The supplementary initiator composition can comprise the same or similar reactants as those comprising the reactant composition to be initiated by the igniter.

In certain embodiments, the supplementary initiator composition can comprise additive materials to facilitate processing, to enhance the mechanical integrity, and/or to determine the burn and spark-generating characteristics (for example and not by way of limitation). An inert additive material will not react or will react to a minimal extent during initiation and burning of the supplementary initiator composition, which is particularly advantageous when working with an enclosed system, where minimization of gas build-up is desired. The additive materials can be inorganic materials and can function as binders, adhesives, gelling agents, thixotropic agents, and/or surfactants. Examples of gelling agents include, but are not limited to, clays such as Laponite®, Montmorillonite, Cloisite®; metal alkoxides such as those represented by the formula R—Si(OR)$_n$ and M(OR)$_n$ (where n can be 3 or 4, and M can be Ti, Zr, Al, B, or other metals); and colloidal particles based on metal hydroxides or oxides. Examples of binding agents include, but are not limited to, soluble silicates such as Na- or K-silicates, aluminum silicates, metal alkoxides, phosphates, inorganic polyanions, inorganic polycations, and inorganic sol-gel materials, such as alumina or silica-based sols. Other useful additive materials include glass beads, diatomaceous earth, nitrocellulose, polyvinylalcohol, guar gum, ethyl cellulose, cellulose acetate, polyvinylpyrrolidone, fluoro-carbon rubber (Viton), and other polymers that can function as a binder. In certain embodiments, the supplementary initiator composition can comprise more than one additive material.

The components of the supplementary initiator composition comprising the oxidizing agent, metal-containing reducing agent, and/or additive material, and/or any appropriate water-soluble or organic-soluble binder, can be mixed by any appropriate physical or mechanical method to achieve a useful level of dispersion and/or homogeneity. For ease of handling, use, and/or coating, the supplementary initiator compositions can be prepared as liquid suspensions or slurries in an organic or aqueous solvent.

The ratio of oxidizing agent to metal-containing reducing agent in the supplementary initiator composition can be selected to determine the appropriate burn and spark-generating characteristics. In certain embodiments, the supplementary initiator composition can be formulated to maximize the production of sparks having sufficient energy to actuate a reactant composition. Sparks emitted from the supplementary initiator composition can impinge upon the surface of the reactant composition, causing the reactant composition to actuate in a self-sustaining exothermic oxidation-reduction reaction.

One way of measuring the power of a supplementary initiator composition is to monitor the temperature on the surface of the substrate. As the properties of the sparks are determined by the supplementary initiator's chemical composition, the assumption is that increased power correlates to higher substrate temperatures. The appropriate amount of each component can be determined based on the stoichiometry of the chemical reaction and the known limitations of energy desired, and/or by routine experimentation. The power can be optimized to deliver sufficient energy to actuate the reactant composition, but not so strong as to damage the reactant composition if it is coated as a thin layer on a substrate surface.

In certain embodiments, the amount of oxidizing agent can range from 5% by weight to 50% by weight of the total dry weight of the supplementary initiator composition. In certain embodiments, the amount of metal-containing reducing agent can range from 25% by weight to 90% by weight of the total dry weight of the supplementary initiator composition.

The particle size of the oxidizing agent and the metal-containing reducing agent can be varied to determine the burn rate, with smaller particle sizes selected for a faster burn (see, for example, PCT Publication No. WO 2004/01396, the contents of which are incorporated in their entirety herein). Thus, in some embodiments where faster burn is desired, it is preferable that the particles be nano-sized.

In certain embodiments, such as those where a reactant composition is coated on a substrate, it is desirable that the reactant composition coating not be modified or damaged upon impact of sparks from the supplementary initiator composition. For example, if the sparks are too intense, the reactant coating may delaminate in such a way that the reaction will not propagate as intended.

III. Reactant Coating Compositions

Upon initiation of the conductive layer, heat from the (exothermic) oxidation of the conductive layer composition is generated sufficiently to actuate a reactant composition, e.g., a reactant composition coated substrate. The reactant coating composition is heated to a temperature of at least 300° C. (for example, within the range of about 300° C. to about 700° C.).

The reactant composition being actuated may comprise reactants which are capable of undergoing an exothermic (i.e., heat-generating) chemical reaction upon actuation by the igniter of the present invention. When the igniter is incorporated in a device designed to heat a substrate, a thin coating of such reactants may be deposited as a solid layer on a surface of the substrate.

The thickness and composition of the reactant coating can determine the maximum temperature as well as the temporal and spatial dynamics of the temperature profile produced when the reactant composition is actuated. Studies using thin reactant composition layers having a thickness ranging from 5 µm to 1000 µm (more particularly, within the range of 5 µm to 500 µm) have shown that the maximum temperature reached by a substrate on which the reactant composition is disposed depends on the thickness of the layer as well as the composition of the reactant composition constituents. For example, for a given reactant coating thickness, one reactant coating composition may reach a different (i.e., higher or lower) maximum temperature than another reactant coating having a different composition, due to the differences in reaction kinetics between the two chemical compositions Maintaining uniformity of the reactant coating composition layer is desirable to achieve uniformity of temperature across that region of the substrate on which the reactant composition is disposed. In certain applications, uniform heating of the substrate can provide desired results, such as, for example, facilitating the production of an aerosol comprising a high purity of a drug or pharmaceutical composition, and maximizing the yield of aerosol from the drug initially deposited on the substrate.

In some embodiments for use with the igniter of the present invention, the thickness of the reactant coating composition on the substrate surface is within the range of about 1 μm to about 300 µm; in other embodiments within the range of about 1 µm to about 100 µm; in yet other embodiments within the range of about 1 µm to about 60 µm.

The reactant coating composition can comprise the same or similar reactants as the supplementary initiator composition. As such, the reactants comprising the reactant coating composition are typically energetic materials such as those described above. The energetic materials may comprise at least one oxidizing agent and at least one metal-containing reducing agent.

The oxidizing agent may be oxygen, an oxygen-based gas, a solid oxidizing agent, or a combination thereof. In one embodiment, the oxidizing agent is a metal-containing oxidizing agent, which may comprises a perchlorate, chlorate, metal oxide, or an organic binder. In a particular embodiment, the metal-containing oxidizing agent is a perchlorate or chlorate of an alkali metal or an alkaline earth metal selected from the group consisting of potassium perchlorate ($KClO_4$), potassium chlorate ($KClO_3$), lithium perchlorate ($LiClO_4$), sodium perchlorate ($NaClO_4$), magnesium perchlorate ($Mg(ClO_4)_2$), and combinations thereof. In another embodiment, the metal-containing oxidizing agent is a metal oxide selected from the group consisting of $MoO_3$, $Fe_2O_3$, $Fe_3O_4$, $V_2O_5$, $CrO_3$, $Cr_2O_3$, $MnO_2$, $CO_3O_4$, $Ag_2O$, $CuO$, $WO_3$, $MgO$, $Nb_2O_5$, $MgAl_2O_4$, $Ce_2O_3$, and combinations thereof. In certain embodiments, the oxidizing agent includes more than one oxidizing agent.

The metal reducing agent may be selected from the group consisting of molybdenum, magnesium, calcium, strontium, barium, boron, titanium, zirconium, vanadium, niobium, tantalum, chromium, tungsten, manganese, iron, cobalt, nickel, copper, zinc, cadmium, tin, antimony, bismuth, aluminum, silicon, and combinations thereof. In some embodiments the metal reducing agent is aluminum, zirconium, titanium, or a combination thereof. In certain embodiments, the metal reducing agent includes more than one metal reducing agent.

Representative examples of reactant coating compositions contemplated for use herein include: $Zr:Fe_2O_3$:Laponite, $Zr:Fe_2O_3:MnO_2$:Laponite, $Zr:CuO$:Laponite, and $Zr:MoO_3$:Laponite. We have found that the addition of an amount of manganese oxide to the fuel material allows for the peak temperature attained by the substrate (e.g., a steel foil) during heating to be modulated, as disclosed in commonly assigned, copending U.S. patent application Ser. No. 12/211,628 filed on even date herewith.

IV. Igniter Configurations

FIGS. 3A-5 illustrate various embodiments of igniter.

Figure 3A:
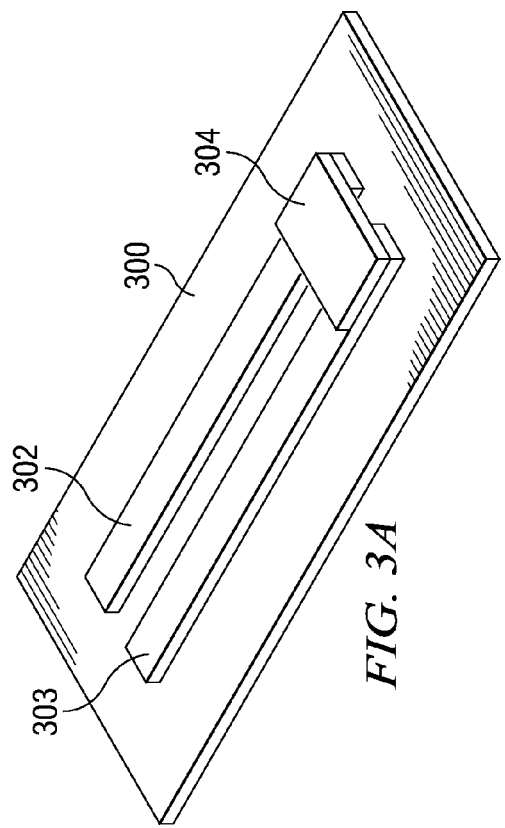

In a basic igniter, shown in FIG. 3A, a conductive layer (in this case, a conductive ink) 304 is printed across two parallel conductors (e.g., electrodes) 302 and 303 on a substrate 300.

Figure 3B:
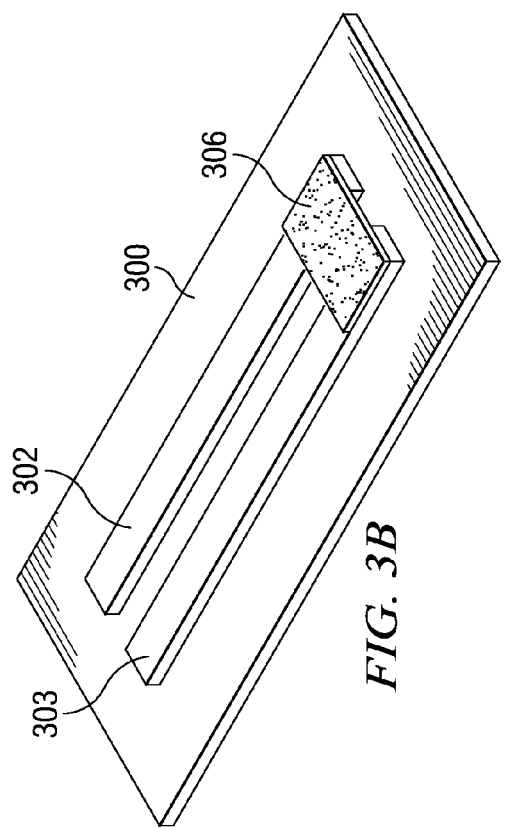

When a supplementary initiator composition is used, the supplementary initiator composition may be admixed with the conductive layer material prior to depositing the conductive layer/initiator composition on the substrate. In this embodiment, the supplementary initiator composition may comprises within the range of about 1% to about 50% of the total weight of the conductive layer/initiator composition. In some embodiments the supplementary initiator composition comprises within the range of about 5% to about 30% of the total weight of the conductive layer/initiator composition. This embodiment of the igniter of the invention is illustrated in FIG. 3B, which shows a conductive ink admixed with a supplementary initiator composition (collectively, 306) printed across two parallel conductors 302 and 303 on a substrate 300.

Figure 3C:
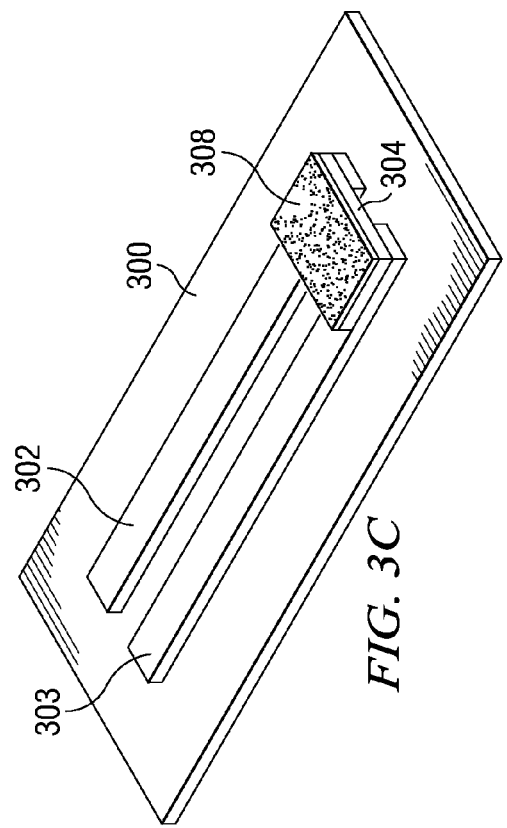
Figure 3D:
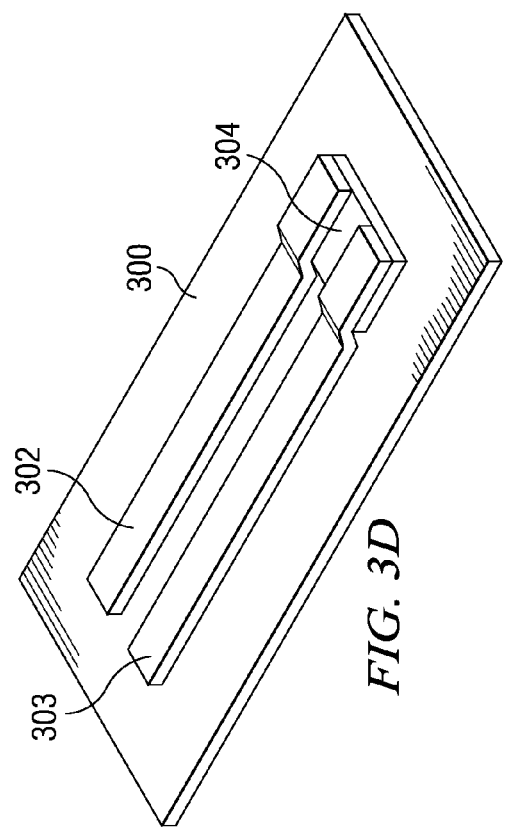

Alternatively, the supplementary initiator composition can be printed as a separate layer over the conductive layer. This embodiment is illustrated in FIG. 3C, which shows a supplementary initiator composition 308 printed across a conductive layer 304, which in turn has been printed across two parallel conductors 302 and 303 on a substrate 300.

Figure 4:
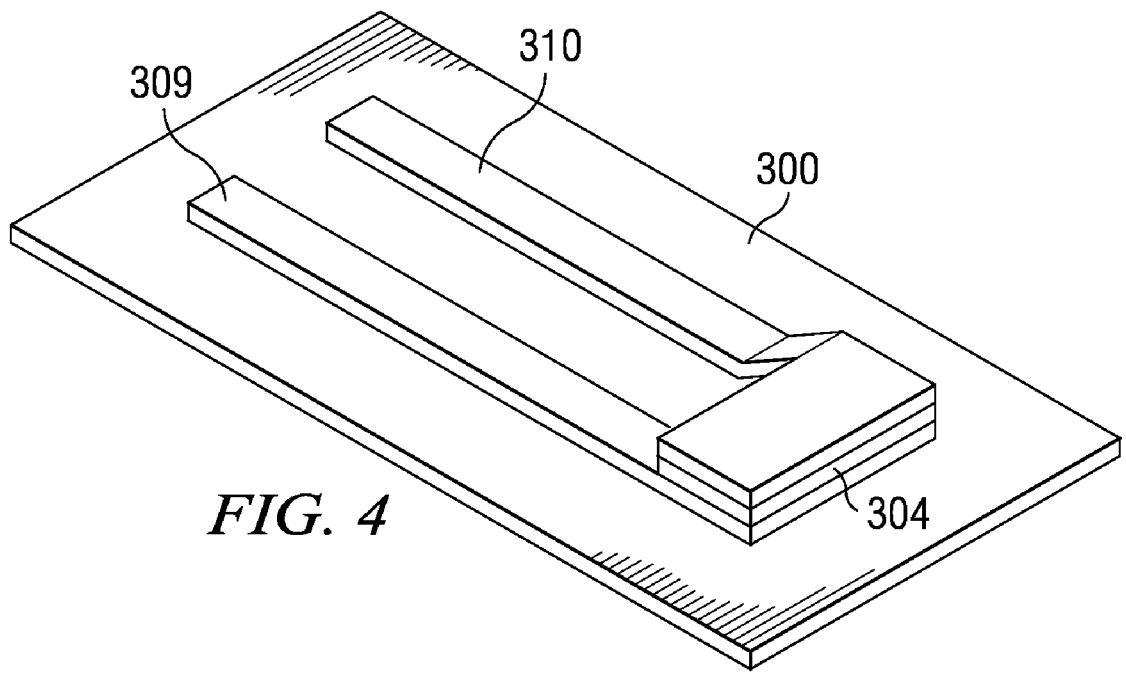

FIG. 4 shows an embodiment of the invention where the conductive layer 304 is sandwiched between two opposing L-shaped electrodes (conductors) 309 and 310 on a substrate 300.

Figure 5:
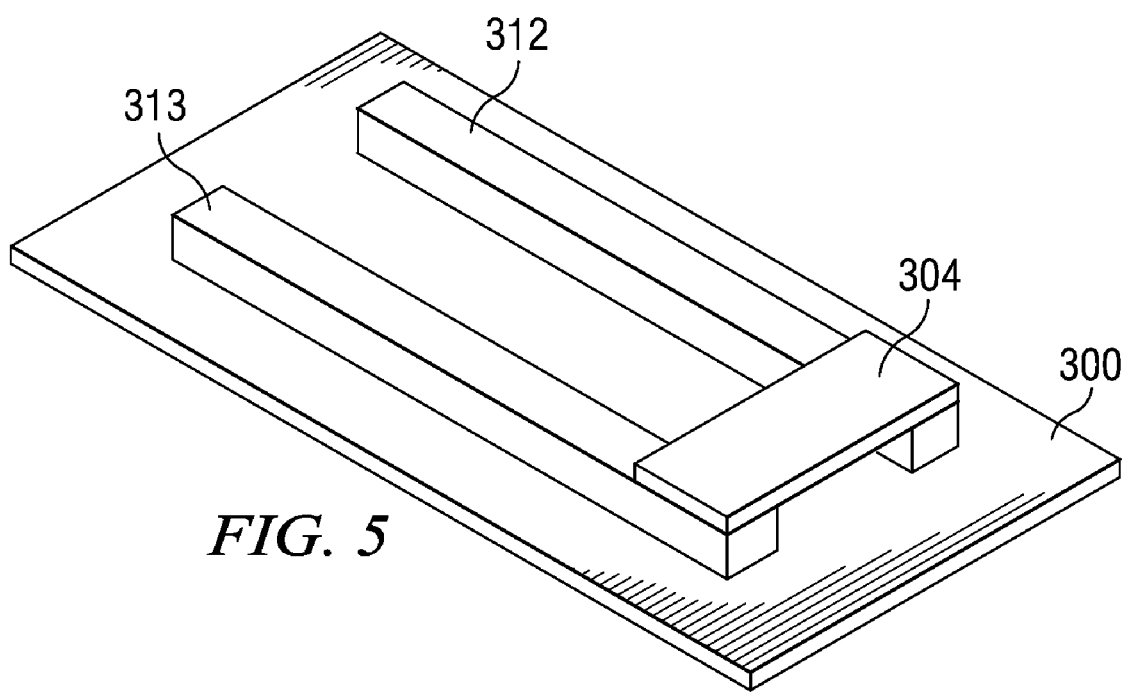

FIG. 5 shows an embodiment of the invention where the two parallel conductors 312 and 313 comprise conductive ink on a substrate 300. Conductive layer 304 overlies conductors 312 and 313. As discussed above, if the conductors and the conductive layer comprise the same conductive ink, the thickness of the conductors (shown as $T_T$ in FIG. 2) should be greater than the thickness of the conductive layer (shown as $T_C$ in FIG. 2), so that the resistance of the conductors 312 and 313 will be less than the resistance of the conductive layer 304.

We have made and tested certain of the igniters described above under various experimental conditions, as described below in the "Examples" section of the present specification. The results indicate that the igniter can be tailored to obtain desired initiation characteristics, including time to initiation, heat generated, voltage required for initiation, and the like, by choice of conductor and conductive layer dimensions, conductive layer resistance, voltage applied, substrate material, presence or absence of supplementary initiator compositions, and the like.

The following results summarize our findings for the specific igniter configurations (e.g., conductive ink containing carbon particles, copper conductors, etc.) and the specific experimental conditions described below. The specific findings will vary with different igniter configurations and experimental conditions. For example, the experimental conditions, conductive ink formulation, coating dimensions, and the nature and format of the reactant coatings determine the voltage and energy requirements of an igniter.

A. Resistance

The resistance of the igniters can be determined using a multi-meter across the at least two conductors. The resistance of the igniters is typically in the range of about 1 Ω to about 70 Ω. The resistance depends on the dimensions of the conductive layer. Referring to FIG. 2, resistance increases with a gap width (W), and decreases with the length (L) and thickness ($T_c$) of the conductive layer.

B. Effect of Dimensions of Conductive Layer

The effects of conductor thickness were investigated using igniters comprising conductive layers formed by printing carbon ink across copper conductors. In several of the examples below, a 1000 µF capacitor was used with a 10 V voltage source, and observed initiation times were found to be in the range of 0.5 to 1 millisecond, consistent with the RC time constant from the capacitor and conductive layer. These values can be adjusted to suit the need of particular embodiments. For example, the time to initiation can be varied by changing the value of the capacitance, current, or voltage, and the conductive layer resistance (dimensions or material). To determine the effects of the conductive layer dimensions, the energy input is kept constant, and all the igniters are initiated using 10 V and a 1000 µF capacitor.

By keeping the thickness of the conductive layer constant and reducing the gap width, both the amount of carbon ink between the conductors and the resistance can be reduced.

C. Effect of Conductor Thickness

The effects of conductor thickness were investigated using igniters comprising conductive layers formed by printing carbon ink across copper conductors. Varying the thickness of the conductors (1 μm and 4 μm) does not appreciably change the resistance or energy required. The internal resistance of copper is so low that the small difference in the thickness is likely to be insignificant. However, it is possible that a significant increase or decrease in the thickness of conductors (without a corresponding decrease or increase in conductor surface area) could affect the internal resistance of the conductors, which could have consequences on igniter design (i.e., the internal resistance of the conductors is a function of the total amount of material comprising the conductors.) Furthermore, if the conductors comprise a conductive ink with high internal resistance (such as, for example, silver ink), the energy requirements of the igniter could be increased.

D. Effect of Substrate Thickness

The effects of the substrate thickness were investigated for polyester substrates having a thickness of 5 mil, KAPTON substrates having thicknesses of 2 mil and 5 mil, and FR4 substrates having thicknesses of 3 mil and 5 mil. While the difference in substrate thickness does not appreciably change the energy required, it can affect the intensity of the glow.

E. Glow Intensity (or Heat Output)

Generally, the intensity of the glow appears to increase with the voltage input. The igniters typically have a minimum voltage requirement below which a glow is not produced. Some igniters have a maximum voltage requirement, above which a glow is not produced; these igniters are typically those that do not employ a supplementary initiator.

F. Voltage and Energy Requirements to Actuate Reactants

Igniters were used to actuate reactants coated on metallic substrates to determine the voltage requirements with a 1000 μF capacitor by placing the igniters in an effective proximity to the coated reactants. A number of different reactants and substrates were used: 3 mil, 4 mil, T430A, 304 stainless steel foils with iron oxide-based reactants (with/without $MnO_2$) in RD or RDS Laponite.

The glow is a visual manifestation of the localized heating that is occurring and indicates the attainment of temperatures above 300° C., and preferably above 400° C. Furthermore, the glow intensity represents the amount of conductive layer (or the surface area of the conductive layer) that oxidizes or glows in a given time. Therefore, depending upon the auto-ignition characteristics of the reactant composition, the heat output of the printable igniter (and/or glow intensity) can be determined. In some embodiments, the reactants may be initiated under 300° C., in which case the glow may not be critical to initiating the reactants. In some embodiments, the exposure time of the sustainable heat or glow is critical to initiating the reactants. The local heat or glow intensity required to initiate a particular reactant composition can be determined by optimizing the voltage, composition of the conductive layer, configuration of the conductive layer, and reactant composition coating parameters.

The minimum voltage required for the glow is about 7 V, whereas the minimum voltage required to actuate the reactant coating is about 10 V. The voltages required to initiate the glow and to actuate the reactants will, of course, vary with different igniter configurations and experimental conditions.

The experimental conditions, conductive ink formulation, coating dimensions, and the nature and format of the reactant coatings determine the voltage and energy requirements of a igniter. In some embodiments the energy required to actuate the reactant composition is within the range of about 2 mJ to about 200 mJ; in other embodiments within a range of about 2 mJ to about 100 mJ; in other embodiments within the range of about 2 mJ to about 60 mJ.

It should be apparent to one of skill in the art to which the invention belongs that embodiments of the invention can be practiced using different sources of electrical power, such as, for example and without limitation, batteries (alkaline, lithium, printable, rechargeable, etc.), capacitors, and power supplies. Capacitors for use in the present invention may have a capacitance within the range of 10 μF to 2000 μF.

The electrical power necessary for a printable igniter to initiate a reactant coating may also be governed by the sustainable peak temperatures. For example, if the printable igniter reaches a peak temperature of over 400° C., but sustains that temperature for only nanoseconds or microseconds, the igniter may not be able to initiate a reactant coating, because the heat generated by the igniter cannot be effectively/efficiently transferred for any practical application. Therefore, balancing the voltage, electrical current, printable starter resistance, time to reach peak temperature, and sustainability of peak temperature becomes critical for accomplishing targeted ignition application. Ohm's law can be used to determine such parameters for a given resistance and voltage (and capacitance).

G. Voltage Requirements to Actuate Reactants with the Addition of Energetic Materials The minimum voltage required to actuate the reactants can be altered by the addition of energetic materials. For example, the addition of 0.8 μL of energetic materials to the top of igniters with carbon ink printed across 4 μm thick silver ink conductors (electrodes) was investigated. The igniters were printed on 5 mil FR4 substrate with a gap width of 100 μm, carbon ink length of 1.5 mm, and carbon thickness of 8 μm. These igniters were used to conduct experiments to determine the energy required to actuate the reactant. By adding energetic materials, the voltage required to actuate the reactant with a 1000 μF capacitor decreases from 10 V (without energetic materials) to 7.5 V. This suggests that the energy requirements of the igniters can be adjusted by choosing the appropriate combination of energetic materials.

H. Use of Igniters to Actuate Reactants

Different types and dimensions of igniters were selected to actuate reactants using 9 V and 1000 μF capacitor.

With the elimination of the fiberglass shield and hence the air space within the device, flatter devices can be produced, which is important for airway design and hence drug aerosol generation, which is one application for the present igniters.

Other igniter designs and compositions based on the disclosure herein can be provided to obtain igniters having particular desired ignition characteristics, including time to initiation, amount of heat generated, voltage required for initiation, dimensional requirements, and the like.

V. Methods of Manufacturing the Igniter

A process for producing an igniter is provided, comprising the steps of: a) providing at least two conductors in a spaced-apart configuration; and b) providing an electrically conductive layer bridging the conductors, where the conductive layer has an electrical resistance greater than the electrical resistance of the conductors, and where the conductive layer is adapted to initiate upon application of electrical power.

The process can further comprise the step of providing a supplementary initiator composition in contact with at least a portion of the conductive layer. The conductive layer and/or conductors may be provided (for example, on a substrate) by a printing operation, which includes but is not limited to, a printing process, stamping, etching, drawing, brushing and painting. In one embodiment the printing operation is a printing process selected from inkjet printing, flexography, offset printing, gravure printing, screen printing, tip dispensing, pad printing (i.e., stamping), Meyer Bar, electrophotographic printing, or lithography. The process can further comprise providing a voltage source in electrical contact with the at least two conductors, and a switch to actuate the igniter.

The igniter can be prepared using manufacturing methods used to prepare printed circuit boards, or can be printed on the substrate using conventional printing techniques known in the art. See, for example, U.S. Pat. Nos. 4,369,269; 4,443,495; 4,508,755; 5,407,473; 6,322,620; 6,537,359; and 7,037,447, which are hereby incorporated by reference in their entireties In certain embodiments, the igniter includes a power source, e.g., a battery, in contact with the at least two conductors. In a particular embodiment, the battery is printed on the substrate.

In another embodiment, an igniter is prepared by providing at least two conductors in a spaced-apart configuration, followed by printing a conductive layer comprising a conductive ink across the conductors. See FIG. 3A.

In an alternative embodiment, an igniter is prepared by printing a conductive layer comprising a conductive ink, followed by providing at least two conductors in a spaced-apart configuration overlying the conductive layer, such that the conductive layer is in contact with the at least two conductors.

In another embodiment, an igniter is prepared by providing at least two conductors in a spaced-apart configuration, followed by printing a conductive layer comprising a mixture of a conductive ink and a supplementary initiator composition (e.g., energetic materials) across the conductors. See FIG. 3B.

In yet another embodiment, an igniter comprising a supplementary initiator composition is prepared by providing at least two conductors in a spaced-apart configuration, printing a conductive layer comprising conductive ink across the conductors, followed by providing a supplementary initiator composition on top of the conductive ink. See FIG. 3C.

In an additional embodiment, an igniter is prepared in which a conductive layer is sandwiched between conductors by first providing at least one conductor, printing a conductive layer comprising conductive ink across the at least one conductor, followed by providing at least one conductor on top of the conductive layer. See FIG. 4.

In yet another embodiment, an igniter consisting essentially of conductive ink and a substrate can be prepared by printing a conductive ink to form at least two conductors in a spaced-apart configuration, and printing a conductive ink across the conductors to form a conductive layer, where the resistance of the conductive layer is higher than the resistance of both of the conductors. See FIG. 5.

One or more components of the igniter may be in contact with a substrate. For example, one or more of the at least two conductors may be in contact with the substrate, then the conductive layer printed over the at least two conductors. Alternatively, the conductive layer may be printed on the substrate, then the at least two conductors placed over the conductive layer. See FIG. 3D.

The igniters can also comprise a voltage source, a capacitor, and an actuator, or these components can be supplied in a separate component. In some embodiments, all of the components required for operation of the igniter are printed onto the igniter substrate.

VI. Applications

The igniters described herein can be utilized in any application where actuation of a reactant composition is desired. In certain embodiments, the conductive layer initiates upon application of electrical power, producing sufficient heat to actuate the reactant composition. In other embodiments, the igniter further comprises a supplementary initiator composition, which can be a low-sparking initiator system or a high-sparking initiator system as required for the particular application. Representative applications include methods and devices for aerosolizing a drug, methods for igniting combustible compositions, as well as methods for igniting pyrotechnic devices, inflating airbags, explosive deployment, and the like.

A. Methods and Devices for Aerosolizing a Drug

The igniters described herein can be advantageously used in aerosol drug delivery devices that use heat to vaporize a drug to be delivered via inhalation, such as, but not limited to, those described in commonly assigned U.S. patent application Ser. Nos. 10/861,554 (filed Jun. 3, 2004, now published as US-2005-0268911 on Dec. 8, 2005, and entitled "Multiple Dose Condensation Aerosol Devices and Methods of Forming Condensation Aerosols") and Ser. No. 10/850,895 (filed May 20, 2004, now published as US-2005-0079166 on Apr. 14, 2005, and entitled "Self-Contained Heating Unit and Drug-Supply Unit Employing Same", each of which is incorporated herein by reference in its entirety.

In order to actuate a reactant composition, in particular, a reactant composition coated on a substrate, the igniter delivers sufficient heat to the reactant composition. If the heat produced by the igniter is insufficient, it may be dissipated by thermal conduction before the reactant composition can actuate. Sparks generated by the igniter may damage the surface of the coated reactant composition and result in non-uniform heating of the surface on which the reactant composition is coated. In certain applications, such as heating units for delivery of drugs as condensation aerosols, this non-uniformity of heating can adversely affect the purity of the resultant aerosol. Additionally, it is desirable that these heating units be activated using lower energy for cost reasons and also to provide the capability for activating multiple heating elements with a single battery.

In certain aspects, a method is provided for producing an aerosol of a drug, comprising the steps of: a) providing an igniter comprising: i) at least two conductors in a spaced-apart configuration, and ii) an electrically conductive layer bridging the conductors, where the conductive layer has an electrical resistance greater than the electrical resistance of the conductors; b) providing a drug supply unit having a heating unit comprising an enclosure comprising a substrate having an exterior surface, where a drug is disposed on a portion of the exterior surface, and a reactant composition capable of undergoing an exothermic reaction disposed within the enclosure; c) placing the igniter into an effective proximity with the reactant composition; and d) actuating the reactant composition by initiating the igniter, thereby producing an aerosol of the drug.

The actuation can be triggered by any convenient means, such as a sensor, a timer, or a switch. For example, the sensor can respond to motion, inhalation, vibration, or the like. In one embodiment, the method comprises producing an aerosol of a drug triggered by the inhalation of the human patient.

Figure 6:
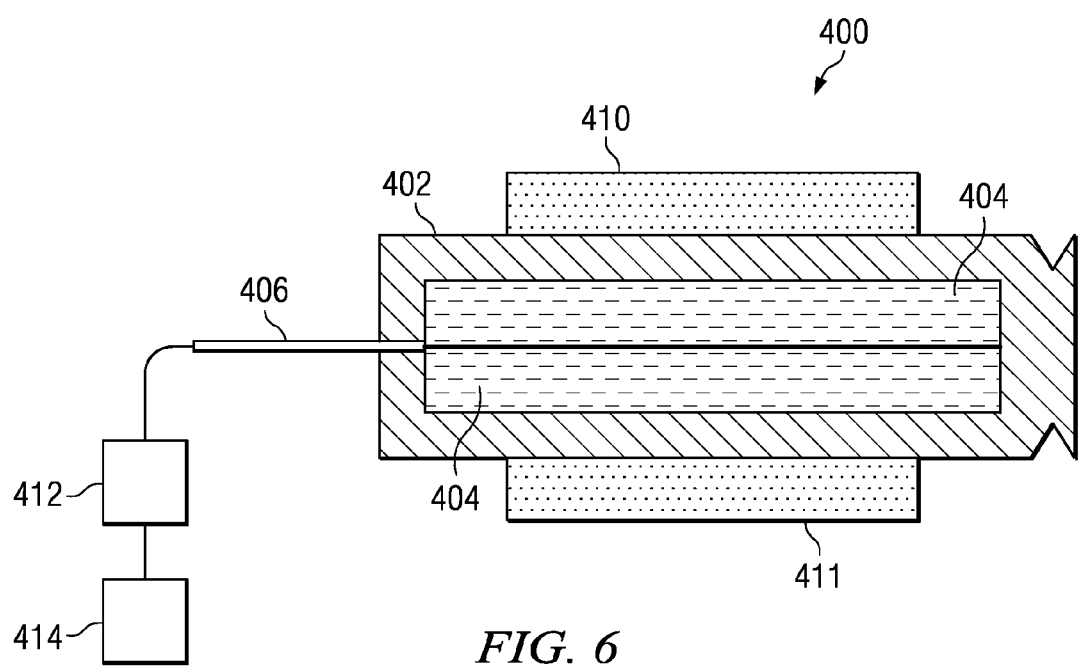

In additional aspects, methods for providing a dose of a drug to a human patient are provided, comprising the steps of: a) providing an igniter comprising: i) at least two conductors in a spaced-apart configuration, and ii) an electrically conductive layer bridging the conductors, where the conductive layer has an electrical resistance greater than the electrical resistance of the conductors; b) providing a drug supply unit having a heating unit comprising an enclosure comprising a substrate having an exterior surface, where a drug is disposed on a portion of the exterior surface, and a reactant composition capable of undergoing an exothermic reduction reaction disposed within the enclosure; c) placing the igniter into an effective proximity with the reactant composition; d) actuation of the reactant composition by initiating the igniter, thereby producing an aerosol of the drug; and e) providing at least one dose of the drug aerosol to the patient. FIG. 6 is a cross-sectional side view of an embodiment of a heating unit described above which includes an igniter and a drug layer coated onto a substrate surface. The heating unit 400 includes a single substrate 402 folded over itself with a chemical reactant material layer 404 deposited on opposing surfaces of the folded-over substrate 402. The heating unit 400 further includes an igniter 406 in effective proximity to ignite the reactant material layer, which may, as illustrated in FIG. 6, include being in contact with reactant layers 404. In other embodiments the igniter need only be in sufficient proximity to, upon ignition, ignite the chemical reactant layer. In this embodiment, the opposing edges of the substrate 402 are seam welded to seal the chemical reactant material layers 404 within the substrate 402. Drug layers 410 and 411 are coated onto the outer (i.e., second) surface of substrate 402. Drug layers 410 and 411 typically comprise the same drug, but may optionally comprise different drugs, as disclosed in commonly assigned, copending U.S. patent application Ser. No. 12/211,247, filed on even date herewith. A voltage source or source of electrical power 414 is in electric communication with the igniter 406. The voltage source 414 could be a battery, power supply or capacitor or any other voltage source. An actuator 412 igniting the igniter is in electric communication with the voltage source and the igniter and could include (for example and not by way of limitation) a sensor which is sensitive to motion, inhalation, vibration or light; a timer; or a switch, which may be a manual switch or an electric switch. The actuation of the device is preferably triggered by inhalation of the patient.

B. Explosive Deployment Devices

The present igniters can also be utilized in any technology utilizing rapid gas generation to deploy a device or execute a particular action. For example, the present igniters can be used in pyrotechnic fasteners, such as explosive bolts, having explosive charges imbedded in the bolt and scored where severance is intended to occur upon detonation, thereby freeing mated units from each other (Pacific Scientific Energetic Materials Co., Hollister, Calif.). Representative technologies utilizing rapid gas generation in device deployment include automobile passenger restraint devices such as airbags, explosive bolts such as those utilized in separation of stages in multistage rockets, ejection devices such as ejection seats, vehicle door openers having explosive hinges for exit in case of accident (U.S. Pat. No. 6,412,584, to Faigle et al.), and the like.

C. Pyrotechnic Devices

The igniters described herein can also be advantageously utilized in the ignition of pyrotechnic devices such as fireworks, munitions, flares, gas generating devices, and the like.

EXAMPLES

In the following examples, efforts have been made to ensure accuracy with respect to numbers used (e.g., amounts, temperature, etc.), but some experimental error and deviation should be accounted for. Unless indicated otherwise, temperature is in degrees Celsius, and pressure is at or near atmospheric.

Igniter design and composition were evaluated to determine optimal parameters for initiation (glow) and actuation (reactant). The following parameters were varied: 1) gap width (W); 2) conductive layer length (L); 3) conductive layer thickness ($T_C$); 4) conductor thickness ($T_T$); 5) substrate thickness; 6) conductor composition; and 7) substrate type, along with 8) capacitance and 9) voltage. The performance of printable igniters, with and without the addition of energetic materials on the conductive layer, was tested, as described in the examples below.

The experimental design included test igniters connected in series with an oscilloscope, a power supply, a capacitor, a switch and a phototransistor. The igniter was placed above the phototransistor for detection of the glow indicative of initiation. The capacitance was varied by changing the capacitors; and voltage to the capacitor was varied using a power supply. Resistances were varied by changing the coating dimensions of conductive layer and choice of materials for conductors.

Once the circuit closed, the capacitor discharged, and a peak was visible on the oscilloscope when the igniter glow was detected by the phototransistor. The traces generated by the capacitor, switch, and phototransistor were displayed on the oscilloscope. The energy stored in the capacitor, the energy used in generating the glow from the igniter, and the time interval were obtained from the oscilloscope traces.

Printable igniters were constructed using two different types of conductors: silver conductive ink (CI—1001 Engineered Conductive Materials, Delaware, Ohio) and copper metal (Onanon, Milpitas, Calif.). Carbon ink was used for the conductive layer (CI—2001 Engineered Conductive Materials, Delaware, Ohio). The dimensions of the igniters tested are listed in Table One, below.

TABLE ONE

Dimensions of Printable igniters

| Dimension | Silver Traces | | Copper Traces | |
|---|---|---|---|---|
| Gap Width (μm) | 100, 125 | | 100 | 15, 50 |
| Carbon Length (mm) | 0.5, 0.75, 1, 1.5 | | 0.5, 1, 1.5, 2 | 0.75, 1, 1.5, 1.8 |
| Carbon Thickness (μm) | 5, 7.5, 9, 12.5 | | 7.5 | 8, 12 |
| Conductor Thickness (μm) | 4 | | 4, 20 | 1, 4, 20 |
| Substrate Material | Polyester | FR4 | FR4 | KAPTON |
| Substrate Thickness (mil) | 5 | 3, 5 | 3, 5 | 2, 5 |

To produce the printable igniters studied, the conductors were screen-printed or plated on a substrate, followed by printing of a conductive layer comprising carbon ink across the conductors.

Example One

Igniter Design Varying the Gap Width of the Conductive Layer

Igniters were prepared with carbon ink (conductive layer) printed across 4 μm thick silver metal conductors on 5 mil polyester substrates with a gap width of 125 μm, carbon thickness of 7.5 μm, and carbon length of 1.5 mm. These igniters were used to conduct the experiments described above (1000 μF capacitor) to determine the lowest voltage required to obtain the glow (self-ignition). The phototransistor detected the glow at 7 V. These igniters were compared with ones with the same dimensions, but with a smaller gap width (100 μm).

By reducing the gap width, both the amount of carbon ink in between the conductors and resistance was reduced, as was the voltage required, which decreased from 7 V to 6V.

Example Two

Igniter Designs Varying the Length of the Conductive Layer

Igniters with carbon ink (conductive layer) printed across 4 μm thick silver ink conductors on 5 mil FR4 substrates were prepared with a gap width of 100 μm, carbon thickness of 7.5 μm, and carbon length of 1.5 mm. The length of the carbon ink varied, and lengths of 1.0, 0.75, and 0.5 mm were used to conduct the experiments described above (1000 μF capacitor) to determine the lowest voltage required to obtain the self-ignition.

By reducing the carbon length, despite the increase in resistance, the voltage required to initiate the igniters with 1000 μF capacitor dropped from 7 V (1.5 mm) to 5.5 V (0.5 mm).

Example Three

Igniter Design Varying the Thickness of the Conductive Layer

Igniters with carbon ink (conductive layer) printed across 4 μm thick silver ink conductors on 5 mil polyester substrates were prepared with a gap width of 125 μm, carbon length of 1.5 mm, and carbon thickness of 5 and 9 μm. These igniters were used to conduct the experiments described above (1000 μF capacitor) to determine the lowest voltage required to obtain the self-ignition.

By increasing the carbon thickness, despite the decrease in resistance, the voltage required to initiate the igniters with 1000 μF capacitor increased from 7 V (5 μm) to 8 V (9 μm).

Example Four

Igniter Design Varying the Conductor Thickness

Igniters with carbon ink (conductive layer) printed across copper metal conductors having the same gap width (100 μm), carbon thickness (8 μm), and carbon length (1 mm) on 5 mil FR4 substrates were prepared and used to investigate the effect of varying the copper conductor thickness (4 and 20 μm) utilizing the experiment described above (1000 μF capacitor).

The difference in copper conductor thickness did not change the resistance and the amount of energy required under the above test conditions.

Example Five

Igniter Design Varying the Thickness of the Substrate

Igniters with carbon ink (conductive layer) printed across 4 μm thick copper metal conductors on both 2 and 5 mil KAPTON substrates were prepared with a gap width of 50 μm, carbon thickness of 8 μm, and carbon length of 0.75 mm. These igniters were used to investigate the effect of varying the thickness of the substrate (2 and 5 mil KAPTON) utilizing the experiment described above (1000 μF capacitor).

The difference in substrate thickness did not change the amount of energy required under the above test conditions.

Example Six

Igniter Design Varying Conductor and Substrate Parameters

Four different types of igniters were prepared having the following parameters:

1) Copper metal conductors (4 μm thick) on 5 mil KAPTON, with a gap width of 50 μm, carbon thickness of 8 μm, and carbon length of 1 mm;

2) Copper metal conductors (4 μm thick) on 2 mil KAPTON, with a gap width of 50 μm, carbon thickness of 8 μm, and carbon length of 1 mm;

3) Copper metal conductors (20 μm thick) on 5 mil FR4, with a gap width of 100 μm, carbon thickness of 8 μm, and carbon length of 1 mm; and 4) Silver ink conductors (4 μm thick) on 5 mil FR4, with a gap width of 100 μm, carbon thickness of 7.5 μm, and carbon length of 1 mm.

All four igniters were prepared with carbon ink (conductive layer) printed across the conductors. The igniters were used to actuate solid reactants using 9 V and 1000 μF capacitor.

All four types of igniters successfully actuated the solid reactant.

Example Seven

Igniter Design Including Energetic Materials

The addition of energetic materials to the conductive layer was tested by depositing 0.8 mL of energetic materials (75 Zr/25 KClO$_4$ in Ethyl Cellulose/Hydroxypropyl Cellulose) on top of igniters with carbon ink (conductive layer) printed across 20 μm thick copper metal conductors. The igniters were printed on 5 mil FR4 substrates with a gap width of 100 μm, carbon length of 0.75 mm, and carbon thickness of 8 μm.

The addition of energetic materials lowered the voltage required to actuate the reactant from 8.5 V to 6.5 V (with 1000 μF capacitor).

Example Eight

Comparative Igniter Design and Performance

Previous generation igniters rely on the spark generated by the energetic materials to actuate the reactant composition. In order to prevent multiple ignitions, a fiberglass shield is required. However, experiments showed that the printable igniters described herein can actuate the reactant without the addition of energetic materials. Therefore, the printable igniter requires fewer components (no energetic materials and hence no fiberglass shield) and produces a more controlled ignition.

Figure 1B:
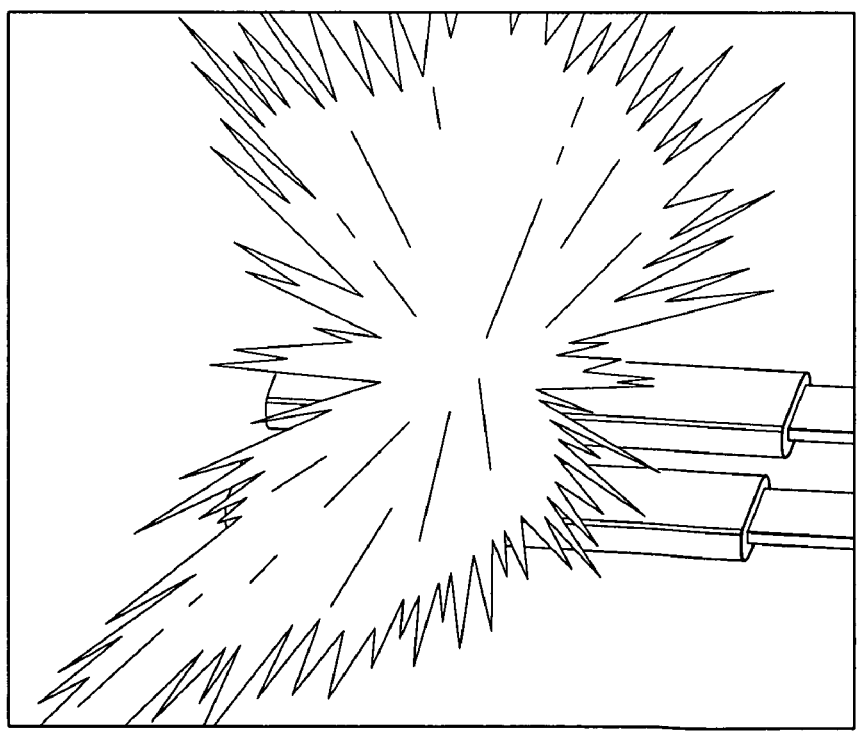

Since the actuation of the reactant by the printable igniters relies on the direct contact of the glow (initiated conductive layer) and reactant, the printable igniter produces a localized heat initiation (as shown in FIG. 1A), while the previous generation igniters produce multiple sparks (as shown in FIG. 1B) and actuate the reactant composition at multiple sites and in a delocalized manner. All igniters tested in Example 6, for example, produce a localized heat initiation, as shown in FIG.

1A, and therefore do not require the presence of a heat shield to protect against flying sparks.

Example Nine

Initiation with 3.0 V Alkaline Batteries

Igniters with carbon ink (conductive layer) printed across 4 μm thick silver ink conductors on 5 mil FR4 substrates were prepared with a gap width of 100 μm, carbon thickness of 7.5 μm, and carbon length of 0.75 mm. Upon initiation by two 1.5 V alkaline batteries, these printable igniters undergo delayed (1-2 second) self-ignition.

Example Ten

Ranges of Resistances

Igniters with carbon ink (conductive layer) printed across 4 μm thick silver ink conductors on 5 mil polyester substrates were prepared with a carbon thickness of 7.5 μm. Resistances ranging from 2 Ω to 75 Ω were able to be initiated by a 3.5 V power supply without any capacitors. As described above, the initiation (glow) was detected by the phototransistor.

Example Eleven

Initiation Energy Requirements Depend on Reactant Composition

Igniters with carbon ink (conductive layer) printed across 4 μm thick silver ink conductors on 5 mil FR4 substrates were prepared with a gap width of 100 μm, carbon thickness of 7.5 μm, and carbon length of 0.75 mm. The lowest voltage required for this configuration to actuate a 66.24 wt. % Zr: 25.76 wt. % $Fe_2O_3$: 8 wt. % $MnO_2$ reactant composition was 8.5 V and 1000 μF capacitor (energy required=36 mJ), while the same configuration of igniters could actuate a different reactant composition (75 Zr/25 $KClO_4$ in Ethyl Cellulose/Hydroxypropyl Cellulose) at 6.5 V and 1000 μF capacitor (energy required=21 mJ).

Example Twelve

Different Voltage Requirements for Glow Initiation and Reactant Actuation

Igniters with carbon ink (conductive layer) printed across 4 μm thick silver ink conductors on 5 mil FR4 substrates were prepared with a gap width of 100 μm, carbon thickness of 7.5 μm, and carbon length of 1.5 mm. The lowest voltage to obtain self-ignition was 7 V and 1000 μF capacitor, while a higher voltage (10 V and 1000 μF capacitor) was required to intensify the glow to actuate the reactant composition (66.24 wt. % Zr: 25.76 wt. % $Fe_2O_3$: 8 wt. % $MnO_2$). Therefore, the glow intensity and the heat output of the printable igniters depend upon the energy supplied.

It is to be understood that while the invention has been described in conjunction with the specific embodiments thereof, that the description above as well as the examples above are intended to illustrate and not limit the scope of the invention. The practice of the present invention will employ, unless otherwise indicated, conventional techniques of chemistry, manufacturing and engineering, and the like, which are within the skill of the art. Other aspects, advantages and modifications within the scope of the invention will be apparent to those skilled in the art to which the invention pertains.

All patents, patent applications, and publications mentioned herein, both supra and infra, are hereby incorporated in their entirety by reference.

We claim:
1. An igniter comprising:
   a) at least two conductors in a spaced-apart configuration, said two conductors comprising a conductive ink, said conductive ink comprising particles in combination with a binder, said particles comprising carbon and wherein said carbon-comprising particles comprise a material selected from the group consisting of carbon, activated carbon, graphite, carbon nanotubes, fullerenes, and combinations thereof; and
   b) an electrically conductive layer bridging said at least two conductors, wherein said conductive layer has an electrical resistance greater than an electrical resistance of said at least two conductors.
2. An igniter comprising:
   a) at least two conductors in a spaced-apart configuration, said at least two conductors comprising a conductive ink, said conductive ink comprising particles in combination with a binder, wherein said conductive ink comprises non-carbon particles; and
   b) an electrically conductive layer bridging said at least two conductors, wherein said conductive layer has an electrical resistance greater than an electrical resistance of said at least two conductors.
3. The igniter of claim 2, wherein said non-carbon particles comprise a metal.
4. An igniter comprising:
   a) at least two conductors in a spaced-apart configuration; and
   b) an electrically conductive layer bridging said at least two conductors, wherein said conductive layer has an electrical resistance greater than an electrical resistance of said at least two conductors, said electrically conductive layer comprising a conductive ink, said conductive ink comprising particles in combination with a binder, wherein said conductive ink comprises non-carbon particles.
5. The igniter of claim 4, wherein said non-carbon particles comprise a metal.
6. An igniter comprising:
   a) at least two conductors in a spaced-apart configuration, said at least two conductors comprising a conductive ink; and
   b) an electrically conductive layer bridging said at least two conductors, wherein said conductive layer has an electrical resistance greater than an electrical resistance of said at least two conductors wherein said conductive layer and said conductors both comprise the same conductive ink, and wherein said conductors have a thickness that is greater than the thickness of said conductive layer.
7. The igniter of claim 6 further comprising a supplementary initiator composition operatively associated with said electrically conductive layer.
8. The igniter of claim 7, wherein said supplementary initiator composition is deposited on said conductive layer.
9. The igniter of claim 8, wherein said conductive layer further comprises said supplementary initiator composition.
10. The igniter of claim 7, wherein said supplementary initiator composition comprises energetic materials.
11. The igniter of claim 7, wherein said supplementary initiator composition comprises at least one oxidizing agent and at least one metal reducing agent.

12. An igniter comprising:
   a) at least two conductors in a spaced-apart configuration;
   b) an electrical conductive layer comprising a conductive ink bridging said at least two conductors, wherein said conductive layer has an electrical resistance greater than an electrical resistance of said at least two conductors; and
   c) a supplementary initiator composition operatively associated with said electrically conductive layer.

13. The igniter of claim 12, wherein said supplementary initiator composition is deposited on said conductive layer.

14. The igniter of claim 12, wherein said conductive layer further comprises said supplementary initiator composition.

15. The igniter of claim 12, wherein said supplementary initiator composition comprises energetic materials.

16. The igniter of claim 15, wherein said supplementary initiator composition comprises at least one oxidizing agent and at least one metal reducing agent.

17. The igniter of claim 16, wherein said oxidizing agent comprises oxygen, an oxygen-based gas, a solid oxidizing agent, and combinations thereof.

18. The igniter of claim 17, wherein said oxidizing agent is a metal-containing oxidizing agent.

19. The igniter of claim 18, wherein said metal-containing oxidizing agent comprises a perchlorate, a chlorate, or a metal oxide.

20. The igniter of claim 19, wherein said metal-containing oxidizing agent is a perchlorate or a chlorate of an alkali metal or an alkaline earth metal.

21. The igniter of claim 20, wherein said metal-containing oxidizing agent is selected from the group consisting of potassium perchlorate ($KClO_4$), potassium chlorate ($KClO_3$), lithium perchlorate ($LiClO_4$), sodium perchlorate ($NaClO_4$), magnesium perchlorate ($Mg(ClO_4)_2$), and combinations thereof.

22. The igniter of claim 18, wherein said metal-containing oxidizing agent is a metal oxide.

23. The igniter of claim 22, wherein said metal oxide is selected from the group consisting of $MoO_3$, $Fe_2O_3$, $Fe_3O_4$, $V_2O_5$, $CrO_3$, $Cr_2O_3$, $MnO_2$, $CO_3O_4$, $Ag_2O$, $CuO$, $WO_3$, $MgO$, $Nb_2O_5$, $MgAl_2O_4$, $Ce_2O_3$, and combinations thereof.

24. The igniter of claim 16, wherein said metal reducing agent is selected from the group consisting of molybdenum, magnesium, calcium, strontium, barium, boron, titanium, zirconium, vanadium, niobium, tantalum, chromium, tungsten, manganese, iron, cobalt, nickel, copper, zinc, cadmium, tin, antimony, bismuth, aluminum, silicon, and combinations thereof.

25. The igniter of claim 24, wherein said metal reducing agent is selected from the group consisting of aluminum, zirconium, titanium, and combinations thereof.

26. The igniter of claim 14 wherein the supplementary initiator composition comprises within the range of about 1% to about 50% of the total weight of the conductive layer/initiator composition.

27. The igniter of claim 14 wherein the supplementary initiator composition comprises within the range of about 5% to about 30% of the total weight of the conductive layer/initiator composition.

28. An igniter comprising:
   a) at least two conductors in a spaced-apart configuration;
   b) an electrically conductive layer bridging said at least two conductors, wherein said conductive layer has an electrical resistance greater than an electrical resistance of said at least two conductors, said conductive layer comprising a conductive ink; and
   c) a supplementary initiator composition operatively associated with said electrically conductive layer.

29. The igniter of claim 28 wherein said conductive layer and said conductors both comprise the same conductive ink, and wherein said conductors have a thickness that is greater than the thickness of said conductive layer.

30. The igniter of claim 28, wherein said supplementary initiator composition is deposited on said conductive layer.

31. The igniter of claim 28, wherein said conductive layer further comprises said supplementary initiator composition.

32. The igniter of claim 28, wherein said supplementary initiator composition comprises energetic materials.

33. The igniter of claim 28, wherein said supplementary initiator composition comprises at least one oxidizing agent and at least one metal reducing agent.

* * * * *